US011446415B2

(12) United States Patent
Takeuchi et al.

(10) Patent No.: US 11,446,415 B2
(45) Date of Patent: Sep. 20, 2022

(54) FLUID CONTROL DEVICE

(71) Applicant: Murata Manufacturing Co., Ltd., Kyoto (JP)

(72) Inventors: Susumu Takeuchi, Kyoto (JP); Kiyoshi Kurihara, Kyoto (JP)

(73) Assignee: MURATA MANUFACTURING CO., LTD., Kyoto (JP)

( * ) Notice: Subject to any disclaimer, the term of this patent is extended or adjusted under 35 U.S.C. 154(b) by 1188 days.

(21) Appl. No.: 15/822,484

(22) Filed: Nov. 27, 2017

(65) Prior Publication Data

US 2018/0071440 A1 Mar. 15, 2018

Related U.S. Application Data

(63) Continuation of application No. PCT/JP2016/065237, filed on May 24, 2016.

(30) Foreign Application Priority Data

May 28, 2015 (JP) .............................. JP2015-108972

(51) Int. Cl.
*A61M 1/00* (2006.01)
*A61F 13/02* (2006.01)
(Continued)

(52) U.S. Cl.
CPC ............ *A61M 1/0001* (2013.01); *A61M 1/74* (2021.05); *A61M 1/784* (2021.05);
(Continued)

(58) Field of Classification Search
CPC ........ A61M 1/00; A61M 13/02; A61M 27/00; A61M 2205/3331; A61M 2205/3337;
(Continued)

(56) References Cited

U.S. PATENT DOCUMENTS

| 4,559,953 | A | 12/1985 | Wright et al. | |
| 4,718,895 | A | 1/1988 | Kurtz et al. | |
| 2008/0015526 | A1* | 1/2008 | Reiner | A61M 1/0001 |
| | | | | 604/320 |

FOREIGN PATENT DOCUMENTS

| CN | 102032445 B | * | 11/2010 |
| JP | S632042 Y2 | | 1/1988 |
| (Continued) | | | |

OTHER PUBLICATIONS

International Search Report for International Application No. PCT/JP2016/065237, dated Jun. 21, 2016.
(Continued)

*Primary Examiner* — Tatyana Zalukaeva
*Assistant Examiner* — Ilya Y Treyger
(74) *Attorney, Agent, or Firm* — Pearne & Gordon LLP

(57) ABSTRACT

A fluid control device includes a container and a passive valve. A vacuum source has a suction hole. The container has a first connection hole, a second connection hole, a third connection hole, a storage chamber, and a water-sealing chamber. The passive valve includes a first valve housing, a second valve housing, and a diaphragm. A ventilation hole, a second ventilation hole, and a third ventilation hole are provided in the first valve housing and the second valve housing. The first ventilation hole of the passive valve communicates with the second connection hole of the container. The second ventilation hole of the passive valve communicates with the suction hole of the vacuum source. The third ventilation hole is opened to the atmosphere. The diaphragm is pinched between the first valve housing and the second valve housing and forms a first region and a second region.

15 Claims, 22 Drawing Sheets

(51) Int. Cl.
*A61M 27/00* (2006.01)
*A61F 13/00* (2006.01)

(52) U.S. Cl.
CPC .............. *A61M 2205/3331* (2013.01); *A61M 2205/3337* (2013.01); *A61M 2205/75* (2013.01); *A61M 2205/7536* (2013.01)

(58) Field of Classification Search
CPC ....... A61M 2205/75; A61M 2205/7536; A61F 13/00; A61B 17/50
See application file for complete search history.

(56) References Cited

FOREIGN PATENT DOCUMENTS

| | | | |
|---|---|---|---|
| JP | H01-26703 | B2 | 5/1989 |
| JP | H04-12984 | B2 | 3/1992 |
| JP | 2587815 | Y2 | 12/1998 |
| JP | 3935340 | B2 | 6/2007 |
| WO | WO2016194564 | A1 * | 5/2015 |

OTHER PUBLICATIONS

Written Opinion for International Application No. PCT/JP2016/065237, dated Jun. 21, 2016.

* cited by examiner

11,446,415 B2

FLUID CONTROL DEVICE

This is a continuation of International Application No. PCT/JP2016/065237 filed on May 24, 2016 which claims priority from Japanese Patent Application No. 2015-108972 filed on May 28, 2015. The contents of these applications are incorporated herein by reference in their entireties.

BACKGROUND OF THE DISCLOSURE

Field of the Disclosure

The present disclosure relates to a fluid control device controlling a flow of fluid.

Description of the Related Art

There has been an existing treatment method for treating an affected part of a subject by applying a negative pressure to the affected part of the subject. With the treatment method, a fluid control device connecting a suction pump to the affected part of the subject is used. For example, Patent Document 1 discloses a medical suction device. The medical suction device includes a body fluid suction tube, an intake tube, a container, a sensor, an air supply tube, a solenoid valve, and a control device.

The container is connected to an affected part of a patient with the body fluid suction tube interposed therebetween. Furthermore, the container is connected to the suction pump with the intake tube interposed therebetween. The container stores therein liquid (blood, pleural effusion, and the like) in fluid that has flowed out from the body of the patient with a suction pressure of the suction pump. The suction pump sucks a gas in the fluid using the intake tube.

The sensor detects a pressure in the container. The air supply tube communicates the inside of the container and the outside air. The solenoid valve is provided in the air supply tube and opens and closes the air supply tube. The control device controls the opening and closing of the solenoid valve based on the pressure in the container, which has been detected by the sensor.

In the above configuration, an excess negative pressure is generated in the container in some cases when the patient coughs or sneezes. In the medical suction device, the control device opens the solenoid valve when the sensor detects the excess negative pressure. With the opening of the solenoid valve, the inside of the container and the outside air communicate with each other and the outside air flows into the container. As a result, the medical suction device can release the excess negative pressure generated in the container.

Patent Document 1: Japanese Unexamined Patent Application Publication No. 2002-65843

BRIEF SUMMARY OF THE DISCLOSURE

The medical suction device in Patent Document 1 is however required to include the sensor for detecting the excess negative pressure, the solenoid valve for taking the outside air into the container, and the control device for controlling the opening and closing of the solenoid valve. The medical suction device in Patent Document 1 therefore has the problems that the structure thereof is complicated and manufacturing cost is increased.

An object of the present disclosure is to provide a fluid control device having a simple structure and the reduced manufacturing cost.

A fluid control device according to an aspect of the present disclosure has the following configuration in order to achieve the above-described object.

The fluid control device in the aspect of the present disclosure includes a container, a pressure resistance portion, and a passive valve. The container has a first connection hole that communicates with an inside of a subject, a storage chamber that stores liquid in fluid which has flowed into the storage chamber through the first connection hole, a second connection hole that communicates with the storage chamber, and a third connection hole that communicates with a suction hole provided in a vacuum source and through which a gas in the fluid flows out. The pressure resistance portion is provided between the storage chamber and the suction hole and generates a difference between an air pressure in the storage chamber and an air pressure in the suction hole.

The passive valve has a valve housing in which a first ventilation hole, a second ventilation hole, and a third ventilation hole are provided, and a diaphragm that forms, in the valve housing, a first region communicating with the first ventilation hole and a second region communicating with the second ventilation hole. The first ventilation hole communicates with the second connection hole, the second ventilation hole communicates with the suction hole, and the third ventilation hole communicates with an outside of the valve housing.

In this configuration, the fluid control device is used as, for example, a drainage. The subject is, for example, a human or an animal. The diaphragm having this configuration passively switches a communication state between the first ventilation hole and the second ventilation hole based on a pressure in the first region and a pressure in the second region. Furthermore, the diaphragm having this configuration passively switches a communication state between the second ventilation hole and the third ventilation hole and a communication state between the first ventilation hole and the third ventilation hole.

In this configuration, when the vacuum source is turned ON, the vacuum source sucks the gas through the suction hole at a predetermined suction pressure. The fluid in the body of the subject is thereby taken into the container through the first connection hole. In the container, liquid (for example, pleural effusion, blood, and the like) of the subject in the fluid that has flowed into the container through the first connection hole is stored in the storage chamber. The gas in the fluid that has flowed into the container through the first connection hole passes through the pressure resistance portion and the third connection hole and is sucked into the vacuum source through the suction hole.

In this case, the pressure resistance portion generates the difference between the air pressure in the storage chamber and the air pressure in the suction hole. With the difference, the pressure in the first region communicating with the storage chamber becomes equal to or higher than the pressure in the second region communicating with the suction hole in the passive valve.

When the subject coughs or sneezes while the vacuum source is in ON state, an excess negative pressure of equal to or higher than the suction pressure is generated in the storage chamber of the container in some cases. In this case, the pressure in the first region communicating with the storage chamber becomes lower than the pressure in the second region communicating with the suction hole in the passive valve.

The diaphragm can thereby passively switch the communication state among the first ventilation hole, the second ventilation hole, and the third ventilation hole using, for example, the case in which the pressure in the first region is equal to or higher than the pressure in the second region and the case in which the pressure in the first region is lower than the pressure in the second region. When, for example, the diaphragm communicates the first ventilation hole, the second ventilation hole, and the third ventilation hole, the air flows in through the third ventilation hole, passes through the passive valve, and rapidly flows into the storage chamber in the container through the first ventilation hole.

The fluid control device configured as described above can therefore release the excess negative pressure even without including a sensor for detecting the excess negative pressure, a solenoid valve for taking the outside air into the container, and a control device for controlling opening and closing of the solenoid valve.

Accordingly, the fluid control device configured as described above has a simple structure and can be reduced in manufacturing cost.

In the aspect of the present disclosure, it is preferable that the diaphragm be fixed to the valve housing so as to:

block communication between the first ventilation hole and the second ventilation hole and block communication between the second ventilation hole and the third ventilation hole when the pressure in the first region is equal to or higher than the pressure in the second region, and communicate the first ventilation hole and the second ventilation hole and communicate the second ventilation hole and the third ventilation hole when the pressure in the first region is lower than the pressure in the second region.

The passive valve having this configuration passively opens and closes a valve based on the pressure in the first region and the pressure in the second region.

In the aspect of the present disclosure, it is preferable that the pressure resistance portion be a water-sealing chamber provided between the storage chamber in the container and the third connection hole.

In this configuration, water is put in the water-sealing chamber. The water-sealing chamber transfers the gas in the fluid that has flowed thereinto through the first connection hole and prevents passage of the liquid by the water. The water-sealing chamber can generate the pressure difference in accordance with the height of a water surface.

In the aspect of the present disclosure, it is preferable that the pressure resistance portion be a valve provided between the third connection hole and the suction hole.

The fluid control device having this configuration generates the pressure difference with not the water-sealing chamber but the valve. Therefore, the fluid control device having this configuration can also be applied to a container including no water-sealing chamber.

In the aspect of the present disclosure, it is preferable that a fourth ventilation hole communicating the second region and the outside of the valve housing be provided in the valve housing.

With this configuration, when an intermittent operation of repeating ON and OFF of the vacuum source is performed for a patient, a small amount of air is taken into the passive valve from the outside of the passive valve through the fourth ventilation hole immediately after the vacuum source is turned OFF. Therefore, a speed at which the diaphragm opens the third ventilation hole is increased in the passive valve. Accordingly, the fluid control device can rapidly release the excess negative pressure immediately after the vacuum source is turned OFF.

It is preferable that the fluid control device in the aspect of the present disclosure include a ventilation path connecting the pressure resistance portion to the suction hole, and a cross-sectional area of the fourth ventilation hole be smaller than a cross-sectional area of the ventilation path.

With this configuration, a small amount of air is taken into the passive valve from the outside of the passive valve through the fourth ventilation hole while the vacuum source is in ON state. However, the suction pressure of the vacuum source is hardly lowered because the cross-sectional area of the ventilation path is small.

It is preferable that the fluid control device in the aspect of the present disclosure further include a filter between the first ventilation hole and the second connection hole.

With this configuration, the air flows in through the third ventilation hole, passes through the passive valve, and rapidly flows into the storage chamber in the container through the first ventilation hole after passing through the filter. In this case, the air passes through the filter and the filter can therefore suck dust and dirt contained in the air. Accordingly, the fluid control device having this configuration can prevent the dust and dirt contained in the air from flowing into the body of the subject.

The present disclosure can provide a fluid control device having a simple structure and reduced in manufacturing cost.

DETAILED DESCRIPTION OF THE DISCLOSURE

Hereinafter, the fluid control device 100 according to a first embodiment of the present disclosure will be described.

Figure 1:
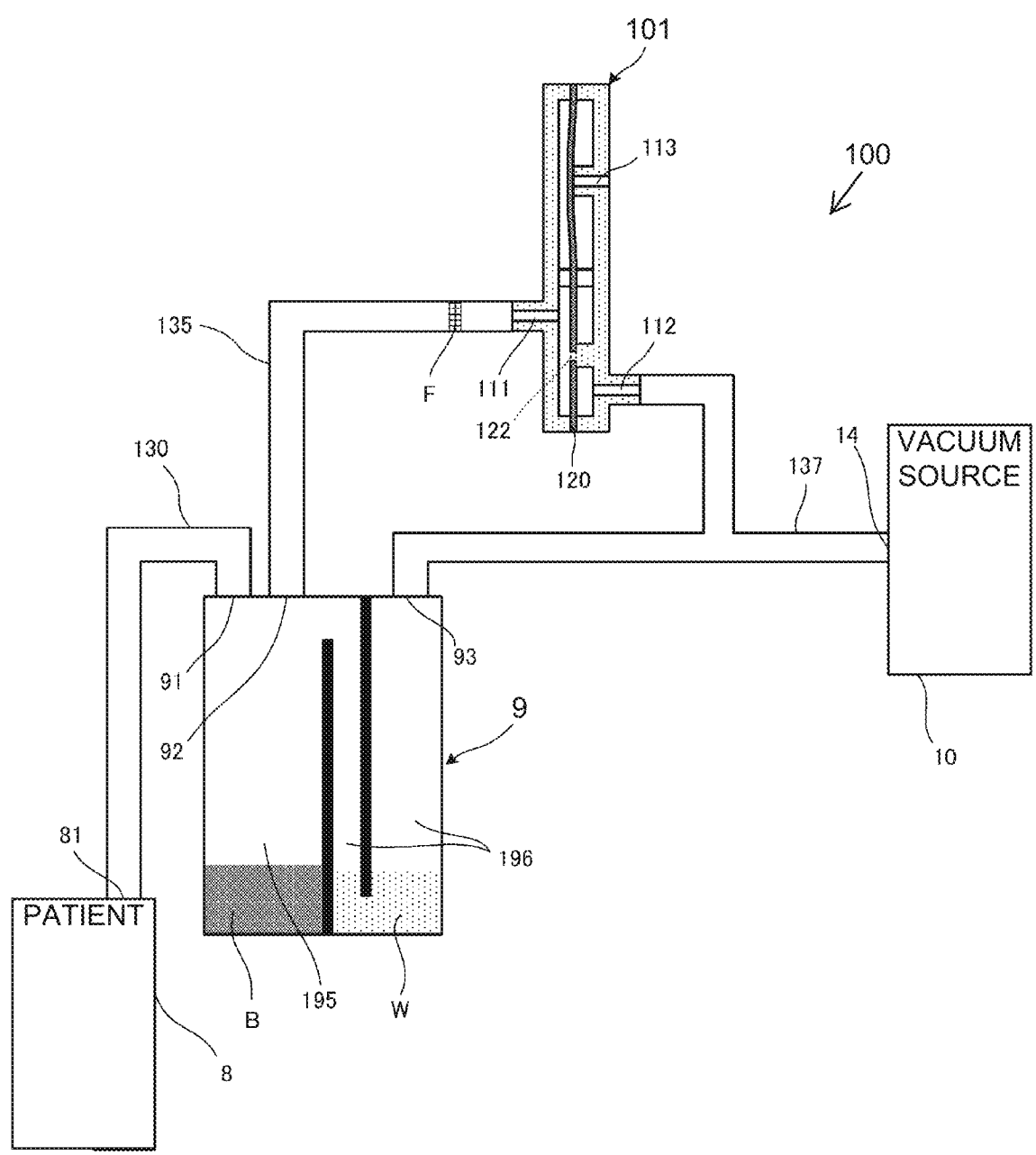
FIG. 1 is a descriptive view for explaining a primary part of a fluid control device 100 according to a first embodiment of the present disclosure.

FIG. 1 is a descriptive view for explaining a primary part of the fluid control device 100 according to the first embodiment of the present disclosure. The fluid control device 100 is a drainage that sucks liquid (for example, pleural effusion, blood, and the like). The fluid control device 100 includes the container 9, the passive valve 101, a tube 130, a tube 135, and a tube 137. The fluid control device 100 is connected to the vacuum source 10 and an affected part of a patient 8.

FIG. 1 illustrates connection manners of the vacuum source 10, the affected part of the patient 8, the container 9, the passive valve 101, the tube 130, the tube 135, and the tube 137 in a simplified manner. In implementation, it is sufficient that they are connected using a desired connection method.

The vacuum source 10 is an appropriate pump and has a suction hole 14 for sucking the air. The vacuum source 10 sucks the air through the suction hole 14 at a predetermined suction pressure.

As will be described in detail later, the passive valve 101 has a first ventilation hole 111, a second ventilation hole 112, and a third ventilation hole 113. The third ventilation hole 113 is opened to the atmosphere.

The container 9 is, for example, a thoracic cavity drain bag. The container 9 has a first connection hole 91, a second connection hole 92, a third connection hole 93, a storage chamber 195, and a water-sealing chamber 196.

It should be noted that the water-sealing chamber 196 corresponds to an example of a "pressure resistance portion" in the present disclosure.

A first terminal of the tube 130 is connected to the first connection hole 91. An intake port 81 as a second terminal of the tube 130 is inserted into the body of the patient 8. Therefore, the inside of the body of the patient 8 communicates with the first connection hole 91 of the container 9 with the tube 130 interposed therebetween.

A first terminal of the tube 135 is connected to the second connection hole 92. A filter F sucking the dust and dirt contained in the air is provided in the tube 135. A second terminal of the tube 135 is connected to the first ventilation hole 111 of the passive valve 101. Therefore, the first ventilation hole 111 of the passive valve 101 communicates with the second connection hole 92 of the container 9.

A first terminal of the tube 137 is connected to the third connection hole 93. A second terminal of the tube 137 is connected to the suction hole 14 of the vacuum source 10. A third terminal of the tube 137 is connected to the second ventilation hole 112 of the passive valve 101. Therefore, the third connection hole 93 of the container 9 communicates with the suction hole 14 of the vacuum source 10. Furthermore, the second ventilation hole 112 of the passive valve 101 communicates with the suction hole 14 of the vacuum source 10.

The storage chamber 195 communicates with the first connection hole 91, the second connection hole 92, and the water-sealing chamber 196. The storage chamber 195 stores therein liquid B (for example, pleural effusion, blood, and the like) of the patient 8 in fluid that has flowed thereinto through the first connection hole 91.

The water-sealing chamber 196 communicates with the storage chamber 195 and the third connection hole 93. Water W is put in the water-sealing chamber 196. The water-sealing chamber 196 transfers the gas in the fluid that has flowed thereinto through the first connection hole 91 and prevents passage of the liquid B with the water W. The air that has passed through the water-sealing chamber 196 flows out to the suction hole 14 of the vacuum source 10 through the third connection hole 93.

Next, the configuration of the passive valve 101 will be described in detail with reference to FIG. 2 to FIG. 4.

Figure 2:
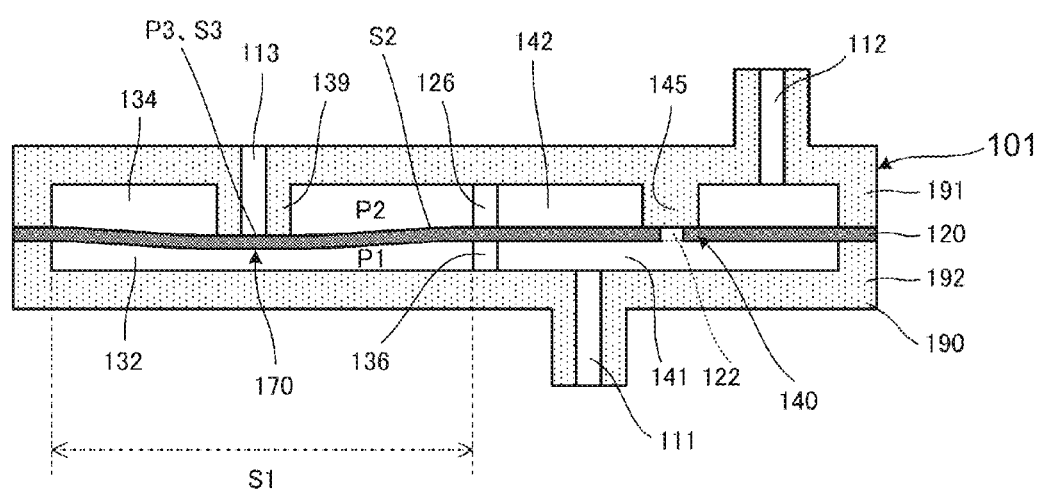
FIG. 2 is a cross-sectional view of a passive valve 101 illustrated in FIG. 1.

FIG. 2 is a cross-sectional view of the passive valve 101 illustrated in FIG. 1. FIG. 3 and FIG. 4 are exploded perspective views of the passive valve 101 illustrated in FIG. 1. FIG. 3 is the exploded perspective view when the passive valve 101 is seen from the upper surface side and FIG. 4 is the exploded perspective view when the passive valve 101 is seen from the bottom surface side.

Figure 3:
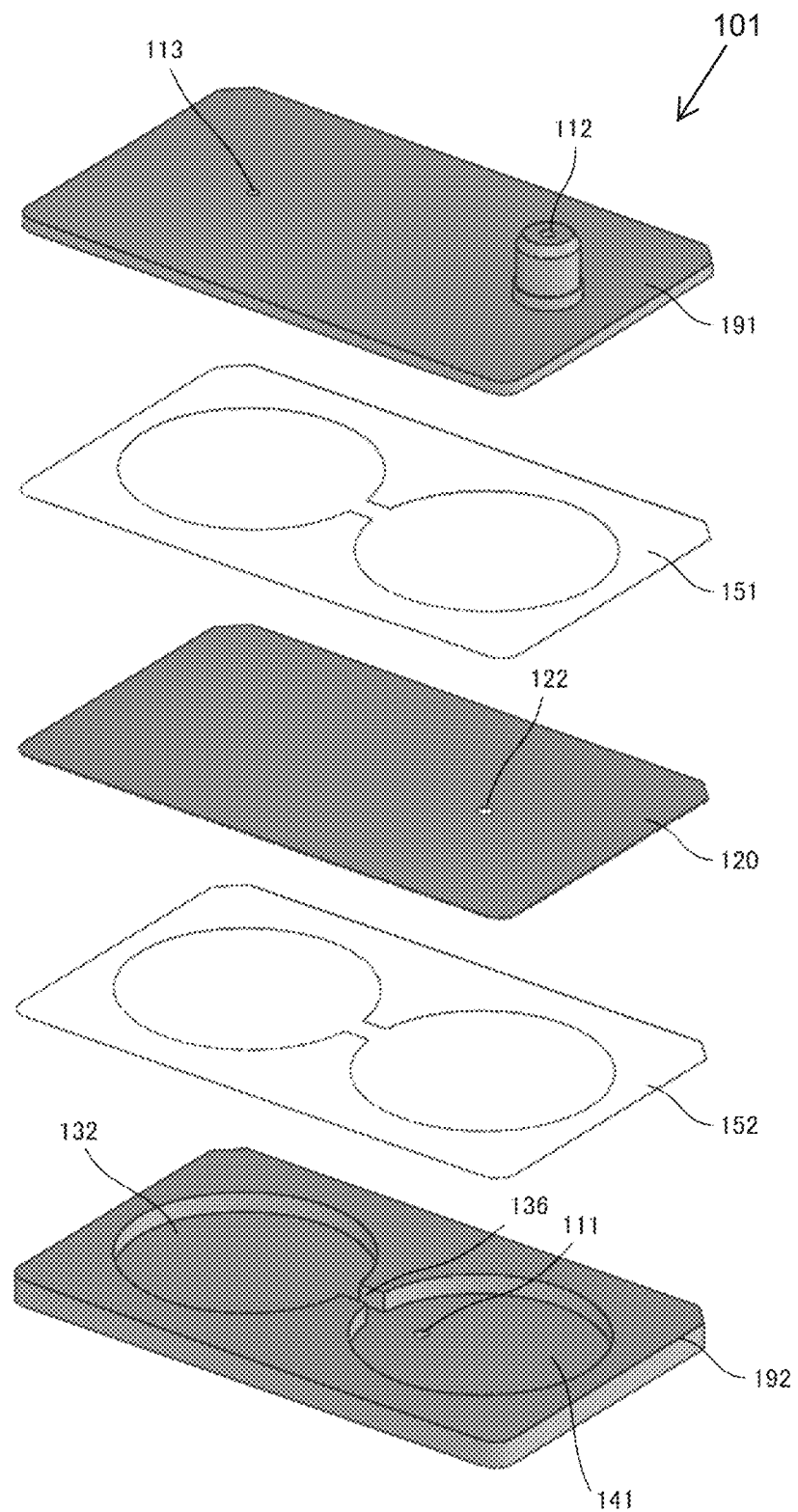
FIG. 3 is an exploded perspective view of the passive valve 101 illustrated in FIG. 1.
Figure 4:
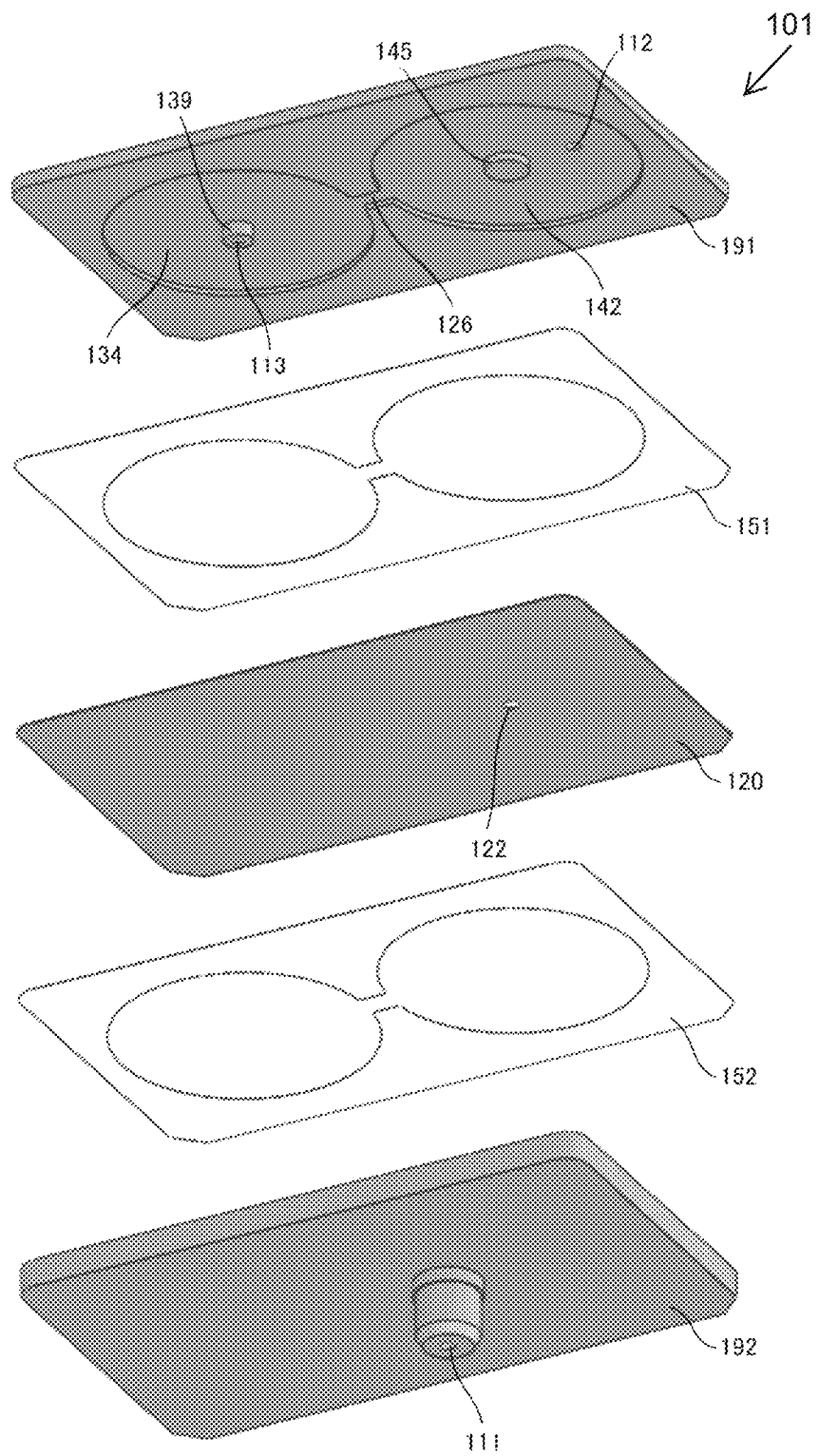
FIG. 4 is an exploded perspective view of the passive valve 101 illustrated in FIG. 1.

As illustrated in FIG. 2 to FIG. 4, the passive valve 101 includes a second valve housing 192, a second seal member 152, a diaphragm 120, a first seal member 151, and a first valve housing 191, and they are laminated in this order. The first valve housing 191 and the second valve housing 192 configure a valve housing 190.

As illustrated in FIG. 2 to FIG. 4, the first valve housing 191 has the second ventilation hole 112 communicating with the suction hole 14 of the vacuum source 10, the third ventilation hole 113 communicating with the outside of the valve housing 190, a valve seat 139 projecting to the diaphragm 120 side from the periphery of the third ventilation hole 113, a columnar valve seat 145 projecting to the diaphragm 120 side, and a communication path 126 communicating an upper valve chamber 142 and an upper valve chamber 134. The first valve housing 191 is made of, for example, resin. The valve seat 139 has a cylindrical shape having the third ventilation hole 113 at a center portion.

As illustrated in FIG. 2 to FIG. 4, the second valve housing 192 has the first ventilation hole 111 communicating with the second connection hole 92 of the container 9 and a communication path 136 communicating a lower valve chamber 141 and a lower valve chamber 132. The second valve housing 192 is made of, for example, resin.

As illustrated in FIG. 2 to FIG. 4, the diaphragm 120 has a circular hole portion 122 at a center portion of a region opposing the valve seat 145. The diameter of the hole portion 122 is set to be smaller than the diameter of the surface of the valve seat 145 abutting against the diaphragm 120.

The diaphragm 120 is formed by a rectangular thin film. A material of the diaphragm 120 is, for example, rubber such as ethylene propylene diene rubber (EPDM) and silicone. The diaphragm 120 is held between the first valve housing 191 and the second valve housing 192 with the first seal member 151 and the second seal member 152 interposed therebetween.

Each of the first seal member 151 and the second seal member 152 is formed by a rectangular thin film. A material of the first seal member 151 and the second seal member 152 is, for example, a both-sided tape or an adhesive. The first seal member 151 has a connection hole in a region facing the upper valve chamber 142, the communication path 126, and the upper valve chamber 134. The second seal member 152 has a connection hole in a region facing the lower valve chamber 141, the communication path 136, and the lower valve chamber 132.

As illustrated in FIG. 2, the diaphragm 120 is fixed to the first valve housing 191 and the second valve housing 192 such that a part of the diaphragm 120 makes contact with the valve seat 139 and the periphery of the hole portion 122 in the diaphragm 120 makes contact with the valve seat 145. In this case, the valve seat 145 pressurizes the periphery of the hole portion 122 in the diaphragm 120.

The diaphragm 120 is fixed to the first valve housing 191 and the second valve housing 192 to thereby divide the inside of the first valve housing 191 and the second valve housing 192. With this configuration, the diaphragm 120 configures the columnar lower valve chamber 141, the columnar lower valve chamber 132, the columnar upper valve chamber 142, and the ring-like upper valve chamber 134 in the first valve housing 191 and the second valve housing 192.

The lower valve chamber 141 communicates with the first ventilation hole 111. The lower valve chamber 132 communicates with the lower valve chamber 141 with the communication path 136 interposed therebetween. The upper valve chamber 142 communicates with the second ventilation hole 112. The upper valve chamber 134 communicates with the upper valve chamber 142 with the communication path 126 interposed therebetween.

The lower valve chamber 141, the communication path 136, and the lower valve chamber 132 correspond to an example of a "first region" in the present disclosure. The upper valve chamber 142, the communication path 126, and the upper valve chamber 134 correspond to an example of a "second region" in the present disclosure.

Furthermore, the diaphragm 120 configures a check valve 140 together with the first valve housing 191 and the second valve housing 192. The check valve 140 is configured by the lower valve chamber 141, the upper valve chamber 142, the valve seat 145, and a region of the diaphragm 120 facing the lower valve chamber 141 and the upper valve chamber 142.

Furthermore, the diaphragm 120 configures an exhaust valve 170 together with the first valve housing 191 and the second valve housing 192. The exhaust valve 170 is configured by the lower valve chamber 132, the upper valve chamber 134, the valve seat 139, and a region of the diaphragm 120 facing the lower valve chamber 132 and the upper valve chamber 134.

In the check valve 140, the diaphragm 120 makes contact with or is separated from the valve seat 145 depending on the pressure difference between the lower valve chamber 141 and the upper valve chamber 142. The check valve 140 thereby allows a flow of the air to the lower valve chamber 141 from the upper valve chamber 142 and blocks the flow of the air to the upper valve chamber 142 from the lower valve chamber 141.

As illustrated in FIG. 2, in the exhaust valve 170, when a relation of S1×(P1−P2)>S3×(P3−P1) is satisfied in which the area of a portion of the diaphragm 120 facing the lower valve chamber 132 is S1, the pressure in the lower valve chamber 132 is P1, the area of a portion of the diaphragm 120 facing the upper valve chamber 134 is S2, the pressure in the upper valve chamber 134 is P2, the area of a portion of the diaphragm 120 facing the third ventilation hole 113 is S3, and the pressure in the third ventilation hole 113 (in the embodiment, an atmospheric pressure) is P3, the diaphragm 120 makes contact with the valve seat 139. By contrast, when S1×(P1−P2) S3×(P3−P1) is satisfied, the diaphragm 120 is separated from the valve seat 139.

Next, a flow of fluid in the fluid control device 100 will be described.

Figure 5:
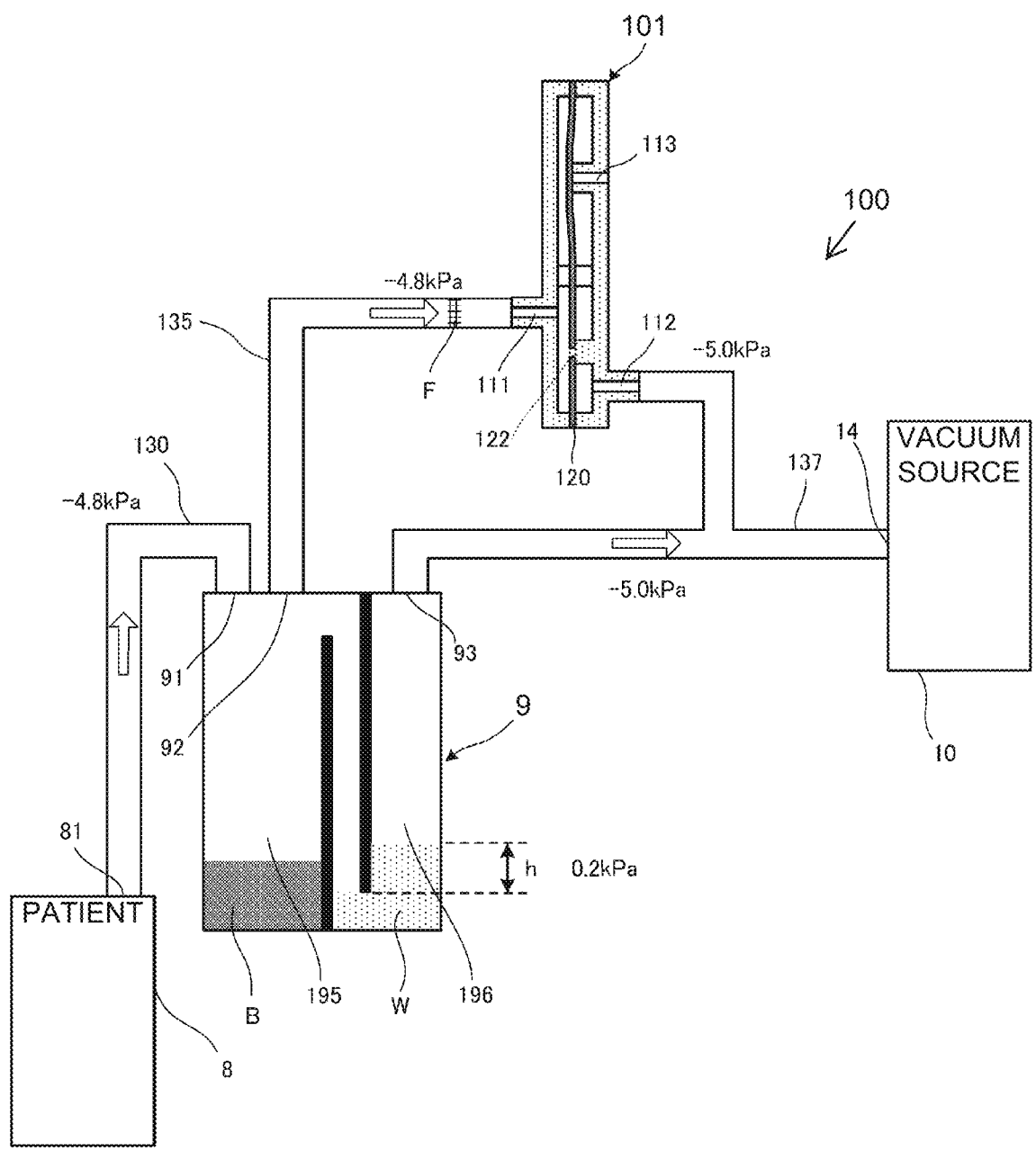
FIG. 5 is a descriptive view for explaining a flow of fluid in the fluid control device 100 while a vacuum source 10 is in ON state.

FIG. 5 is a descriptive view for explaining the flow of fluid in the fluid control device 100 while the vacuum source 10 is in ON state. Arrows in the drawing indicate the flow of the air.

As described above, the lower valve chamber 141, the communication path 136, and the lower valve chamber 132 correspond to the example of the "first region" in the present disclosure. The upper valve chamber 142, the communication path 126, and the upper valve chamber 134 correspond to the example of the "second region" in the present disclosure. The water-sealing chamber 196 corresponds to the example of the "pressure resistance portion" in the present disclosure.

First, a medical worker inserts the intake port 81 of the tube 130 into the body of the patient 8. Then, the medical worker turns ON the vacuum source 10. The pressure in the container 9 before the vacuum source 10 is turned ON is the atmospheric pressure.

When the vacuum source 10 is turned ON, the vacuum source 10 sucks the air through the suction hole 14 at a predetermined suction pressure (for example, −5.0 kPa). With this suction, in the passive valve 101, the air in the upper valve chamber 142 and the upper valve chamber 134 is taken into the vacuum source 10 through the suction hole 14 after passing through the second ventilation hole 112. In the container 9, the gases in the storage chamber 195 and the water-sealing chamber 196 are taken into the vacuum source 10 through the suction hole 14 after passing through the third connection hole 93.

The water-sealing chamber 196 generates a difference between the air pressure in the storage chamber 195 and the air pressure in the suction hole 14. When a height h of the water surface is, for example, 2 cm, the water-sealing chamber 196 generates the difference for a water pressure of 0.2 kPa between the air pressure in the storage chamber 195 and the air pressure in the suction hole 14. This pressure difference generates, for example, a difference in the water pressure of 0.2 kPa between the air pressure in the first region and the air pressure in the second region in the passive valve 101, as illustrated in FIG. 5.

That is to say, in the check valve 140, the pressure in the lower valve chamber 141 is higher than the pressure in the upper valve chamber 142. Therefore, a state in which the periphery of the hole portion 122 in the diaphragm 120 makes contact with the valve seat 145 is kept to block communication between the lower valve chamber 141 and the upper valve chamber 142.

In the exhaust valve 170, the pressure in the lower valve chamber 132 is higher than the pressure in the upper valve chamber 134. Therefore, the diaphragm 120 seals the third ventilation hole 113 to block communication between the upper valve chamber 134 and the third ventilation hole 113.

In the above-described manner, when the pressure in the first region is equal to or higher than the pressure in the second region, the passive valve 101 blocks the communication between the first ventilation hole 111 and the second ventilation hole 112 and blocks the communication between the second ventilation hole 112 and the third ventilation hole 113.

Accordingly, in the fluid control device 100, the fluid in the body of the patient 8 is taken into the container 9 through the intake port 81 while the vacuum source 10 is in ON state. In the container 9, the liquid B (for example, pleural effusion, blood, and the like) of the patient 8 in the fluid that has flowed into the container 9 through the first connection hole 91 is stored in the storage chamber 195. The gas in the fluid that has flowed into the container 9 through the first connection hole 91 passes through the water-sealing chamber 196. Then, the gas that has passed through the water-sealing chamber 196 is sucked into the vacuum source 10 through the suction hole 14 after passing through the third connection hole 93.

Figure 6:
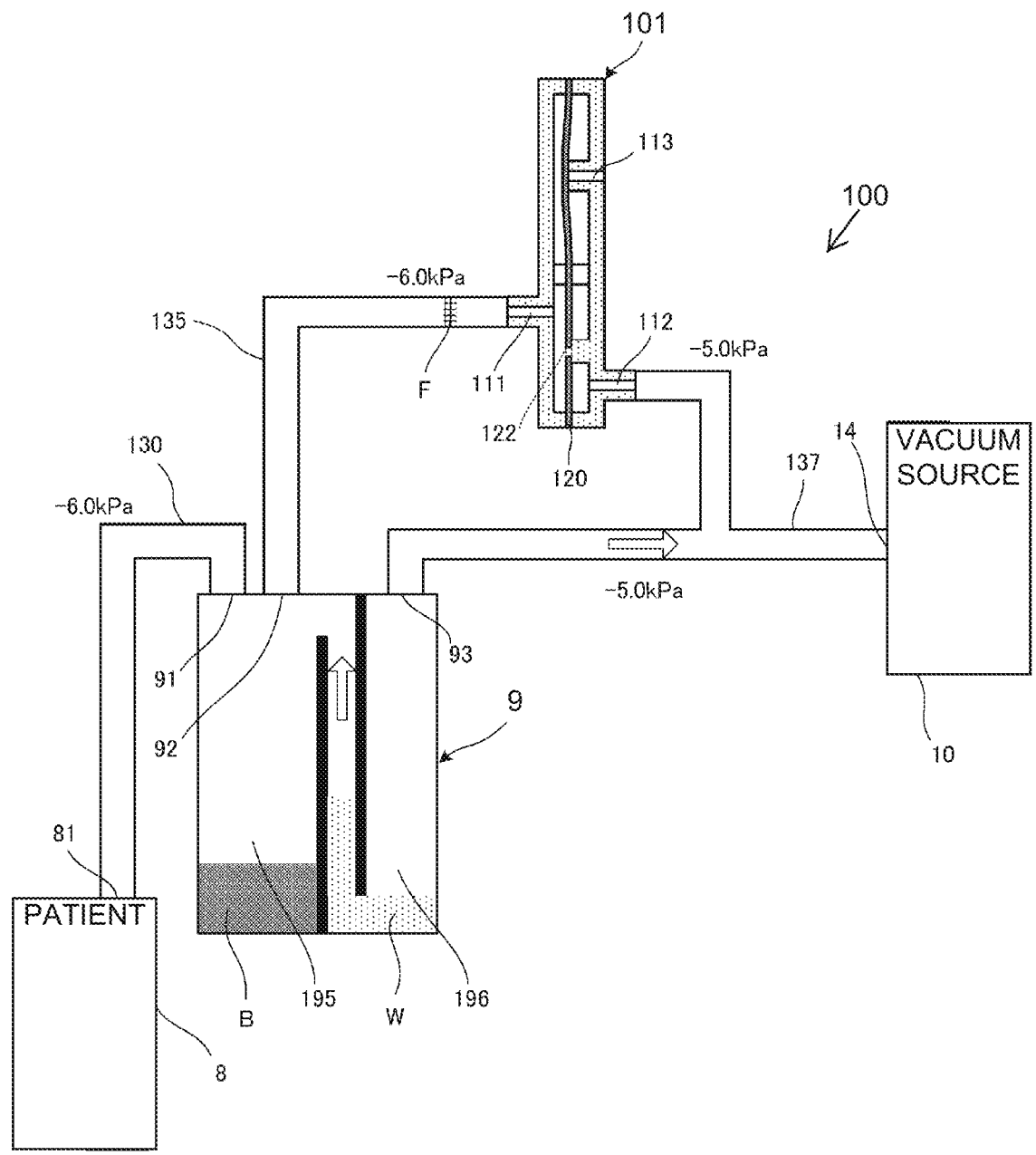
FIG. 6 is a descriptive view for explaining the flow of fluid in the fluid control device 100 at a moment when an excess negative pressure is generated in a container 9.
Figure 7:
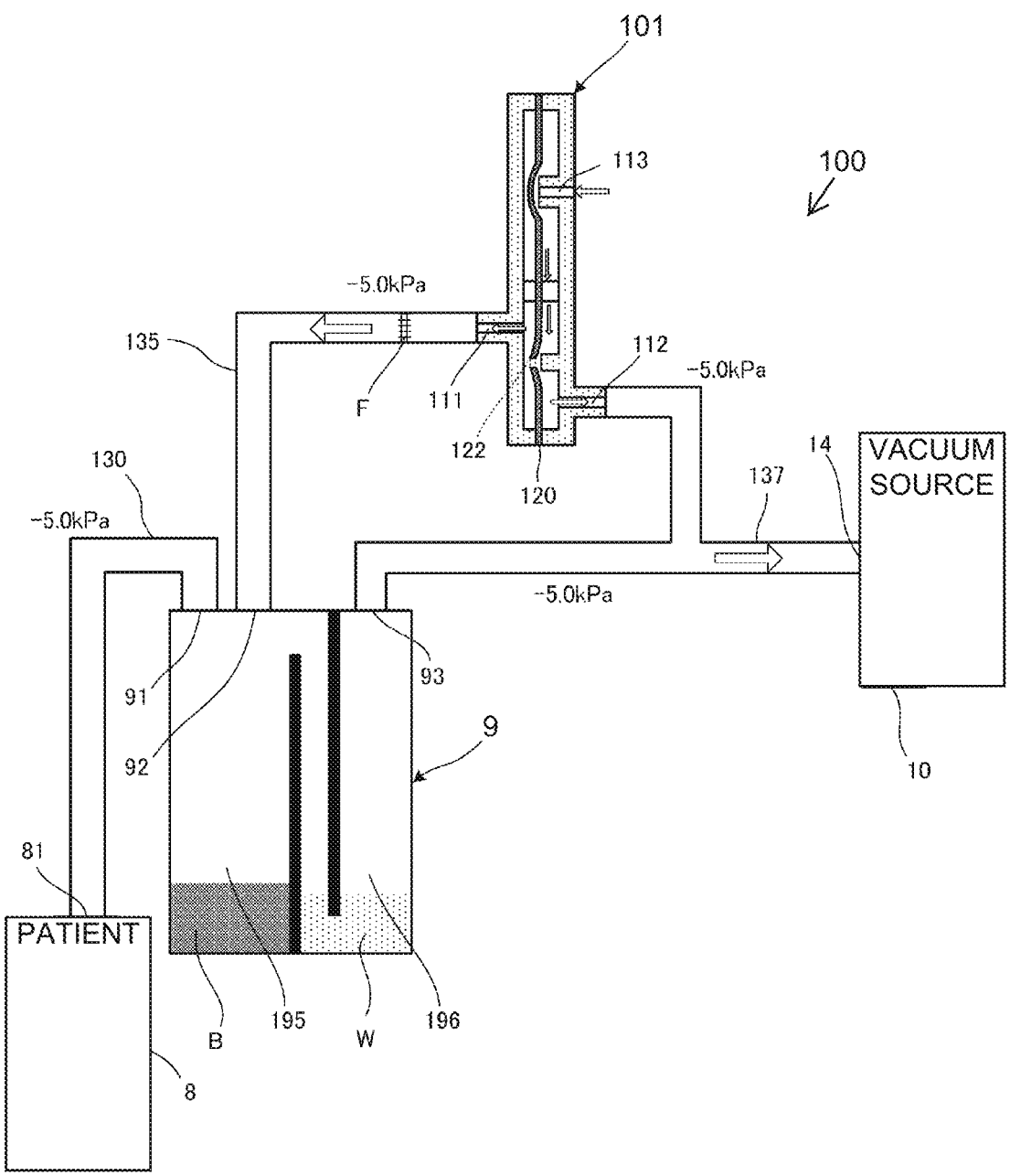
FIG. 7 is a descriptive view for explaining the flow of fluid in the fluid control device 100 immediately after the excess negative pressure is generated in the container 9.
Figure 8:
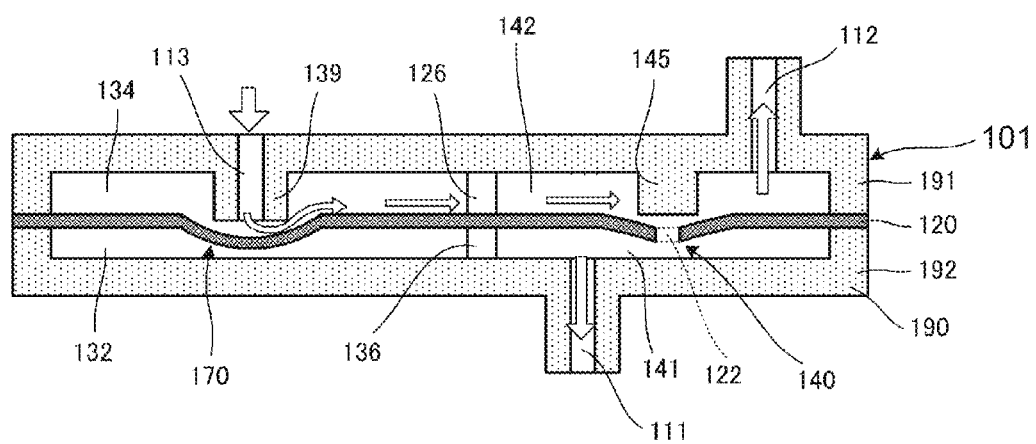
FIG. 8 is a cross-sectional view of the passive valve 101 illustrated in FIG. 7.

FIG. 6 is a descriptive view for explaining the flow of fluid in the fluid control device 100 at a moment when an excess negative pressure is generated in the container 9. FIG. 7 is a descriptive view for explaining the flow of fluid in the fluid control device 100 immediately after the excess negative pressure is generated in the container 9. FIG. 8 is a cross-sectional view of the passive valve 101 illustrated in FIG. 7. Arrows in the drawings indicate the flow of the air.

When the patient 8 coughs or sneezes while the vacuum source 10 is in ON state, an excess negative pressure of equal to or higher than the suction pressure of the vacuum source 10 is generated in the storage chamber 195 of the container 9 in some cases. The excess negative pressure elevates the water W in the water-sealing chamber 196 to the storage chamber 195 side in the container 9, as illustrated in FIG. 6. For example, the air pressure in the storage chamber 195 becomes lower than the air pressure in the suction hole 14 by 1.0 kPa in some cases.

In the check valve 140, the pressure in the lower valve chamber 141 becomes lower than the pressure in the upper valve chamber 142, as illustrated in FIG. 6. Therefore, as illustrated in FIG. 7 and FIG. 8, the periphery of the hole portion 122 in the diaphragm 120 is separated from the valve seat 145 to communicate the lower valve chamber 141 and the upper valve chamber 142.

In the exhaust valve 170, the pressure in the lower valve chamber 132 becomes lower than the pressure in the upper valve chamber 134, as illustrated in FIG. 6. Therefore, as illustrated in FIG. 7 and FIG. 8, the diaphragm 120 is separated from the third ventilation hole 113 to communicate the upper valve chamber 134 and the third ventilation hole 113.

In the above-described manner, when the pressure in the first region is lower than the pressure in the second region, the passive valve 101 communicates the first ventilation hole 111 and the second ventilation hole 112 and communicates the second ventilation hole 112 and the third ventilation hole 113.

Accordingly, the air flows in through the third ventilation hole 113, passes through the upper valve chamber 134, the communication path 126, the upper valve chamber 142, the hole portion 122, and the lower valve chamber 141, and rapidly flows into the storage chamber 195 in the container 9 through the first ventilation hole 111 after passing through the filter F (see FIG. 7 and FIG. 8). In this case, the air passes through the filter F and the filter F can therefore suck dust and dirt contained in the air. This suction can prevent the dust and dirt contained in the air from flowing into the body of the patient 8.

Thereafter, the pressure (air pressure) in the storage chamber 195 is increased to a pressure that is the same as the suction pressure of the vacuum source 10. When the pressure in the storage chamber 195 becomes the pressure that is the same as the suction pressure of the vacuum source 10, the pressure in the first region becomes the same as the pressure in the second region in the passive valve 101.

Therefore, the passive valve 101 blocks the communication between the first ventilation hole 111 and the second ventilation hole 112 and blocks the communication between the second ventilation hole 112 and the third ventilation hole 113. As a result, the flow of fluid returns to the state illustrated in FIG. 5. That is to say, the fluid control device 100 can return the pressure in the storage chamber 195 to the predetermined negative pressure (for example, −4.8 kPa).

With the above-described manner, when the excess negative pressure is generated in the storage chamber 195 in the container 9, in the passive valve 101, the diaphragm 120 automatically opens the check valve 140 and the exhaust valve 170. That is to say, when the excess negative pressure is generated in the storage chamber 195 in the container 9, the passive valve 101 passively opens the check valve 140 and the exhaust valve 170. The fluid control device 100 configured as described above can therefore release the excess negative pressure even without including a sensor for detecting the excess negative pressure, a solenoid valve for taking the outside air into the container 9, and a control device for controlling opening and closing of the solenoid valve.

Accordingly, the fluid control device 100 configured as described above has a simple structure and can therefore be reduced in manufacturing cost.

Furthermore, the medical worker can easily introduce the passive valve 101 into an existing drainage system only by replacing the sensor, the solenoid valve, and the control device included in the existing drainage system by the passive valve 101. Therefore, the fluid control device 100 can reduce introduction cost.

When the passive valve 101 is attacked by bacteria or the like, the medical worker can easily detach the passive valve 101 from the tubes 135 and 137 and replace it by a new one. Therefore, the fluid control device 100 can reduce hospital maintenance cost.

An intermittent operation of repeating ON and OFF of the vacuum source 10 is performed for treatment of the patient 8 in some cases. In this case, immediately after the vacuum source 10 is turned OFF, in the passive valve 101, the air flows into the second region through the suction hole 14 of the vacuum source 10 and the pressure in the first region becomes lower than the pressure in the second region. The passive valve 101 thereby passively opens the check valve 140 and the exhaust valve 170, as illustrated in FIG. 7.

As a result, the fluid control device 100 can release the inside of the container 9 to the atmosphere while the vacuum source 10 is in OFF state. Furthermore, the fluid control device 100 can return the pressure in the storage chamber 195 to the predetermined negative pressure (for example, −4.8 kPa) while the vacuum source 10 is in ON state (see FIG. 5).

With the fluid control device 100 (drainage) illustrated in FIG. 1, when the patient 8 coughs or sneezes while the vacuum source 10 is in ON state, the excess negative pressure of equal to or higher than the suction pressure of the vacuum source 10 is generated in the storage chamber 195 of the container 9 in some cases. In this case, the pressure in the storage chamber 195 is required to be immediately returned to the suction pressure of the vacuum source 10.

However, the pressure in the storage chamber 195 is also minutely lowered due to normal breathing of the patient 8. Frequent opening of the passive valve 101 and return of the pressure in the storage chamber 195 to the suction pressure of the vacuum source 10 every time when the patient 8 normally breathes put a burden on the patient 8.

In consideration of this situation, in the passive valve 101, the dimensions of the valve seat 139 and the valve seat 145 illustrated in FIG. 2 are adjusted. In the passive valve 101, a pressure at which the passive valve 101 is opened can thereby be adjusted. For example, adjustment can be made such that when the patient 8 normally breathes, the passive valve 101 is not opened whereas when the patient 8 coughs or sneezes, the passive valve 101 is opened. With this adjustment, the passive valve 101 can immediately return the pressure in the storage chamber 195 to the suction pressure of the vacuum source 10 only when the patient 8 coughs or sneezes.

Hereinafter, a fluid control device 200 according to a second embodiment of the present disclosure will be described.

Figure 9:
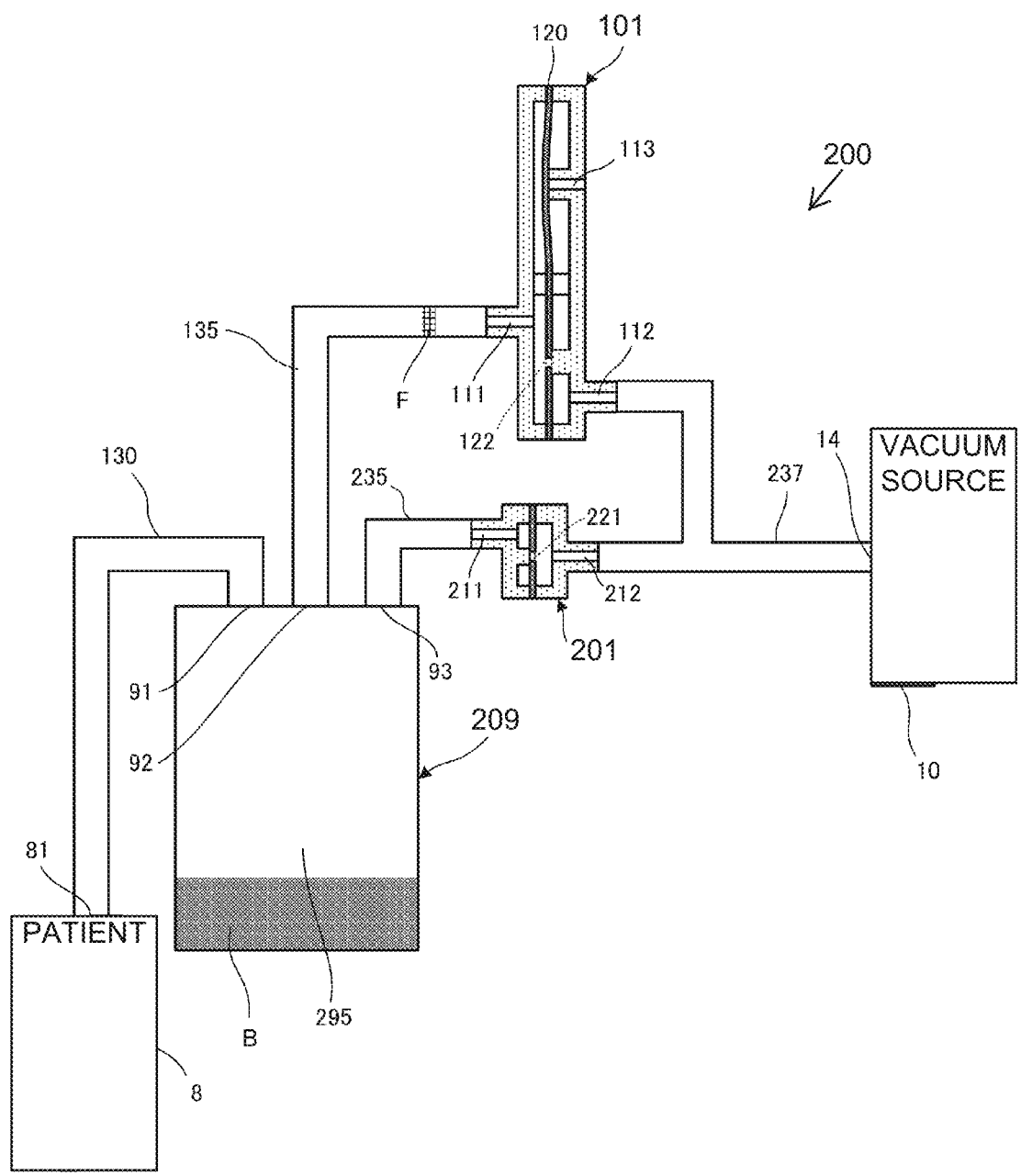
FIG. 9 is a descriptive view for explaining a primary part of a fluid control device 200 according to a second embodiment of the present disclosure.
Figure 10:
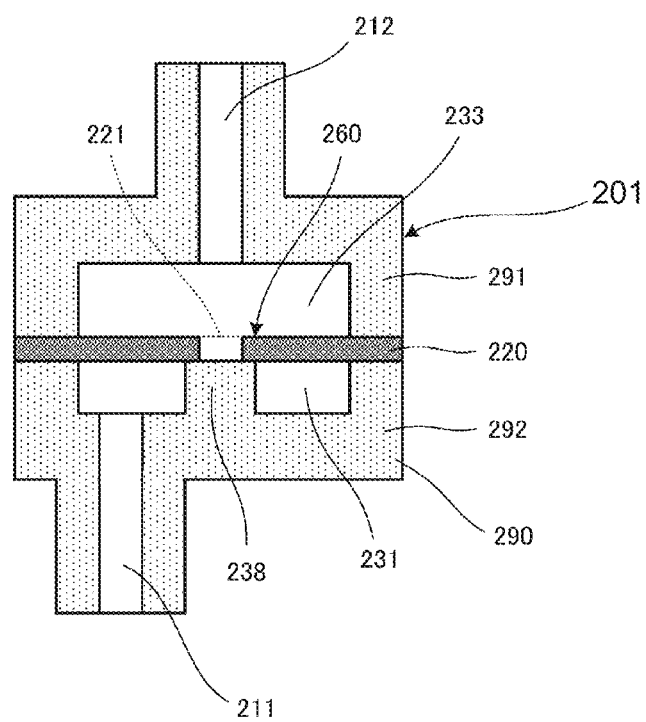
FIG. 10 is a cross-sectional view of a passive valve 201 illustrated in FIG. 9.

FIG. 9 is a descriptive view for explaining a primary part of the fluid control device 200 in the second embodiment of the present disclosure. FIG. 10 is a cross-sectional view of a passive valve 201 illustrated in FIG. 9. The fluid control device 200 is different from the fluid control device 100 in the point that it includes the passive valve 201 instead of the water-sealing chamber 196. Other configurations are the same and the description thereof is therefore omitted.

It should be noted that the passive valve 201 corresponds to an example of the "pressure resistance portion" in the present disclosure.

A container 209 is different from the container 9 in the point that it does not include the water-sealing chamber 196. The container 209 includes the first connection hole 91, the second connection hole 92, the third connection hole 93, and a storage chamber 295.

As illustrated in FIG. 10, the passive valve 201 includes a second valve housing 292, a second seal member (not illustrated), a diaphragm 220, a first seal member (not illustrated), and a first valve housing 291, and they are laminated in this order. The first valve housing 291 and the second valve housing 292 configure a valve housing 290.

The first valve housing 291 has a second ventilation hole 212 communicating with the suction hole 14 of the vacuum source 10. The first valve housing 291 is made of, for example, resin.

The second valve housing 292 has a first ventilation hole 211 communicating with the third connection hole 93 of the container 209 and a columnar valve seat 238 projecting to the diaphragm 220 side. The second valve housing 292 is made of, for example, resin.

The diaphragm 220 has a circular hole portion 221 at a center portion of a region opposing the valve seat 238. The diameter of the hole portion 221 is set to be smaller than the diameter of the surface of the valve seat 238 abutting against the diaphragm 220.

The diaphragm 220 is held between the first valve housing 291 and the second valve housing 292 with the first seal member and the second seal member interposed therebetween. The diaphragm 220 is fixed to the first valve housing 291 and the second valve housing 292 such that a periphery of the hole portion 221 in the diaphragm 220 makes contact with the valve seat 238. In this case, the valve seat 238 pressurizes the periphery of the hole portion 221 in the diaphragm 220.

The diaphragm 220 is fixed to the first valve housing 291 and the second valve housing 292 to thereby divide the inside of the first valve housing 291 and the second valve housing 292. In this manner, the diaphragm 220 configures a ring-like lower valve chamber 231 and a columnar upper valve chamber 233 in the first valve housing 291 and the second valve housing 292.

The diaphragm 220 configures a check valve 260 together with the first valve housing 291 and the second valve housing 292. The check valve 260 is configured by the lower valve chamber 231, the upper valve chamber 233, the valve seat 238, and a region of the diaphragm 220 facing the lower valve chamber 231 and the upper valve chamber 233.

In the check valve 260, the diaphragm 220 makes contact with or is separated from the valve seat 238 depending on a pressure difference between the lower valve chamber 231 and the upper valve chamber 233. The check valve 260 thereby allows a flow of the air to the upper valve chamber 233 from the lower valve chamber 231 and blocks the flow of the air to the lower valve chamber 231 from the upper valve chamber 233.

A first terminal of a tube 235 is connected to the third connection hole 93. A second terminal of the tube 235 is connected to the first ventilation hole 211. A first terminal of a tube 237 is connected to the second ventilation hole 212 of the passive valve 201. A second terminal of the tube 237 is connected to the suction hole 14 of the vacuum source 10. A third terminal of the tube 237 is connected to the second ventilation hole 112 of the passive valve 101.

Next, a flow of fluid in the fluid control device 200 will be described.

Figure 11:
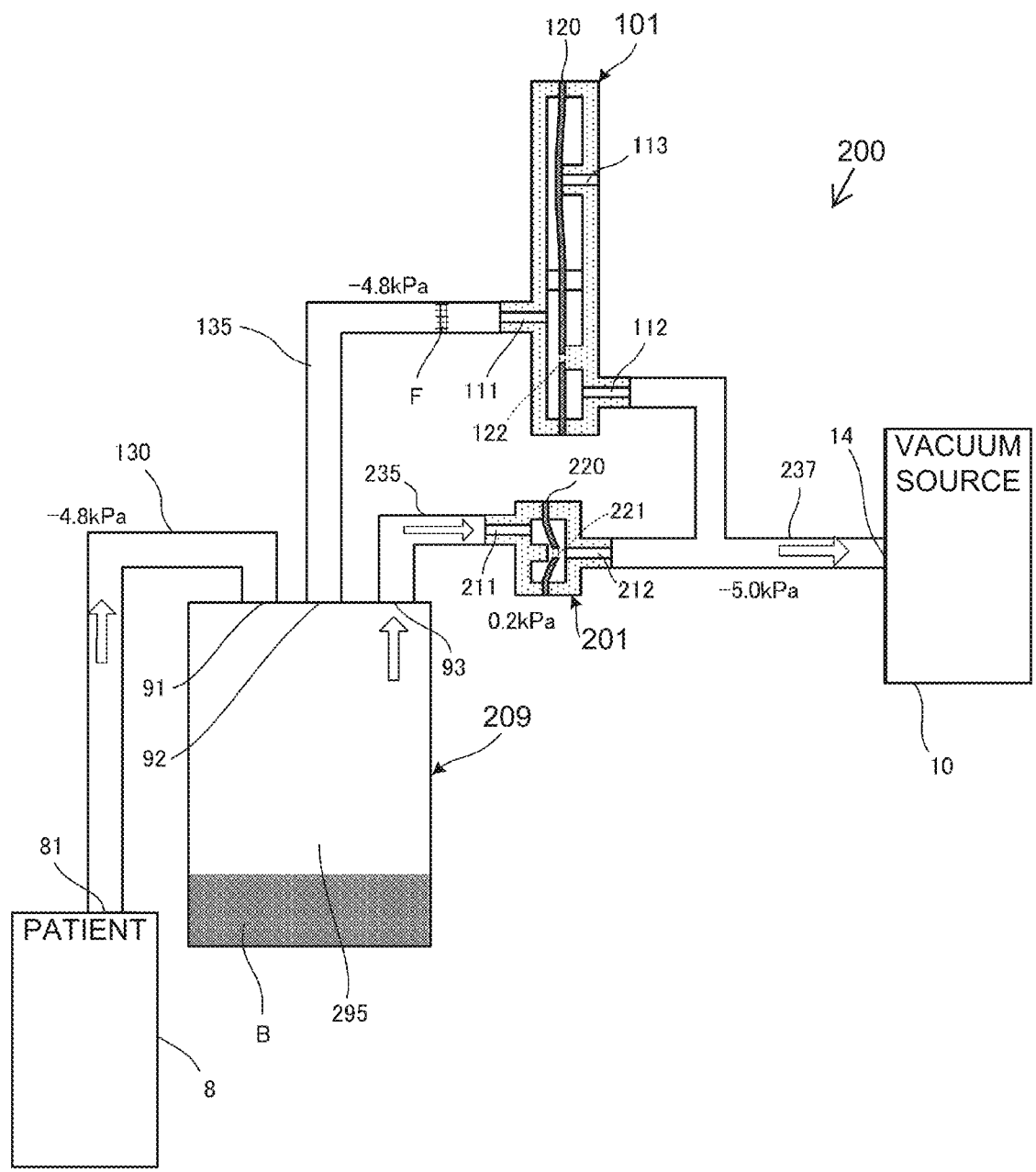
FIG. 11 is a descriptive view for explaining the flow of fluid in the fluid control device 200 while the vacuum source 10 is in ON state.
Figure 12:
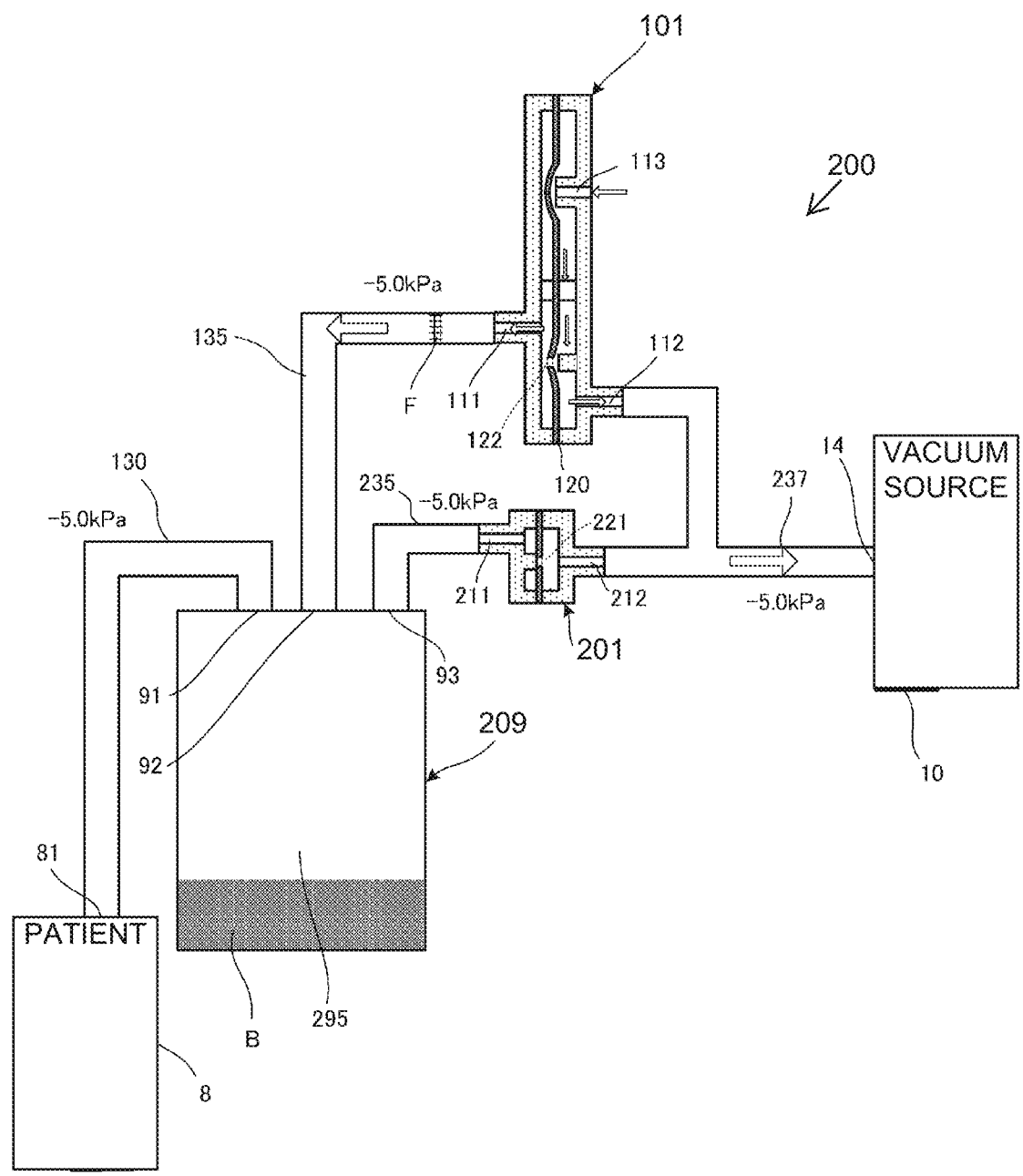
FIG. 12 is a descriptive view for explaining the flow of fluid in the fluid control device 200 immediately after the excess negative pressure is generated in the container 209.

FIG. 11 is a descriptive view for explaining the flow of fluid in the fluid control device 200 while the vacuum source 10 is in ON state. FIG. 12 is a descriptive view for explaining the flow of fluid in the fluid control device 200 immediately after an excess negative pressure is generated in the container 209. Arrows in the drawings indicate the flow of the air.

As illustrated in FIG. 11, the gas that has passed through the storage chamber 295 and has flowed out through the third connection hole 93 is sucked into the vacuum source 10 through the suction hole 14 after passing through the passive valve 201 while the vacuum source 10 is in ON state.

The passive valve 201 generates a difference between an air pressure in the storage chamber 295 and an air pressure in the suction hole 14. For example, when 0.2 kPa is necessary for opening the check valve 260, the passive valve 201 generates a difference of 0.2 kPa between the air pressure in the storage chamber 295 and the air pressure in the suction hole 14. This pressure difference generates, for example, a difference of 0.2 kPa between the air pressure in the first region and the air pressure in the second region in the passive valve 101. Therefore, the fluid control device 200 can also be applied to the container 209 without the water-sealing chamber 196.

As illustrated in FIG. 12, the flow of fluid in the fluid control device 200 immediately after the excess negative pressure is generated in the container 209 is the same as the flow of fluid in the fluid control device 100, which is illustrated in FIG. 7. Accordingly, the fluid control device 200 also provides the same effects as those of the fluid control device 100.

Hereinafter, a fluid control device 300 according to a third embodiment of the present disclosure will be described.

Figure 13:
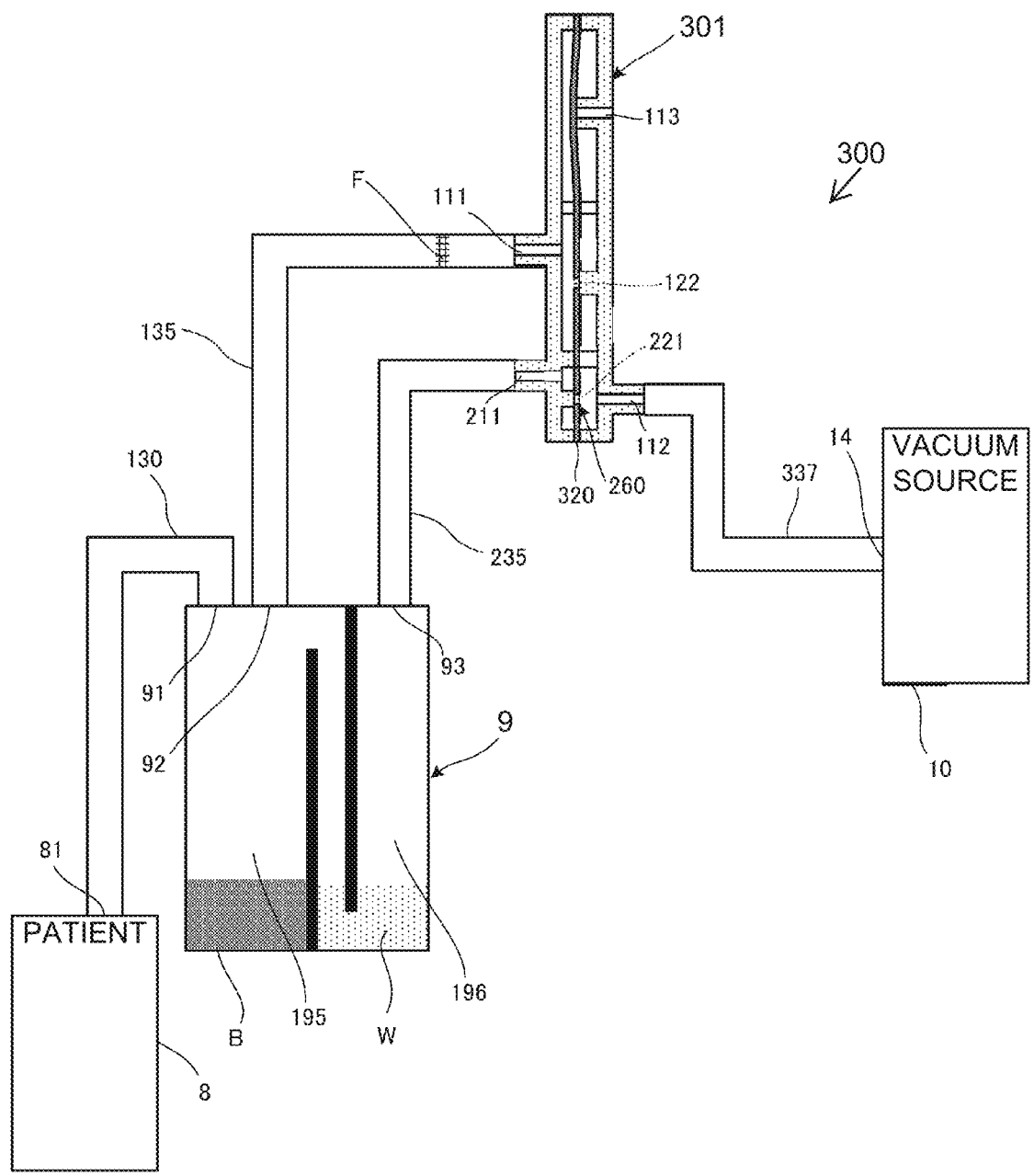
FIG. 13 is a descriptive view for explaining a primary part of a fluid control device 300 according to a third embodiment of the present disclosure.
Figure 14:
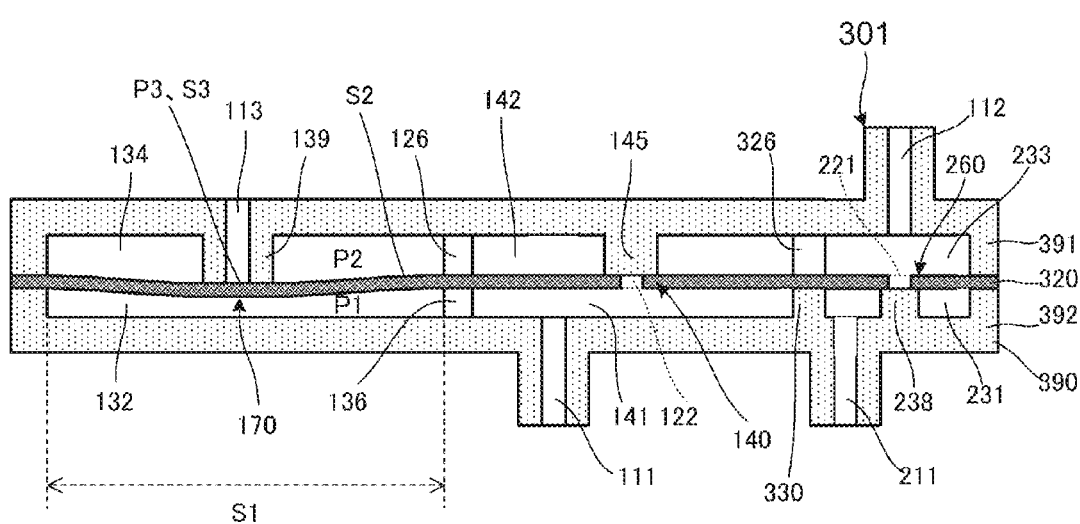
FIG. 14 is a cross-sectional view of a passive valve 301 illustrated in FIG. 13.
Figure 15:
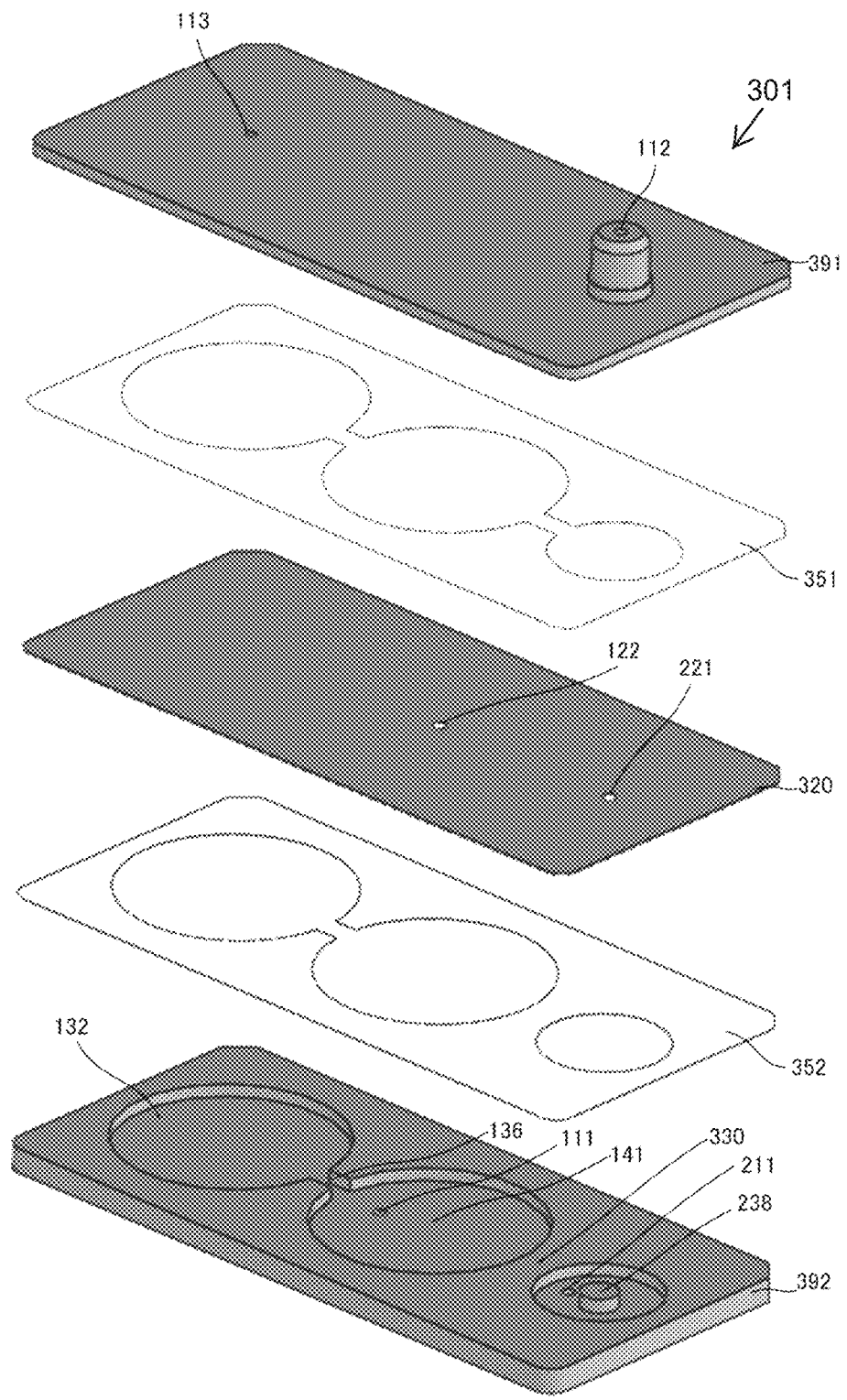
FIG. 15 is an exploded perspective view of the passive valve 301 illustrated in FIG. 13.
Figure 16:
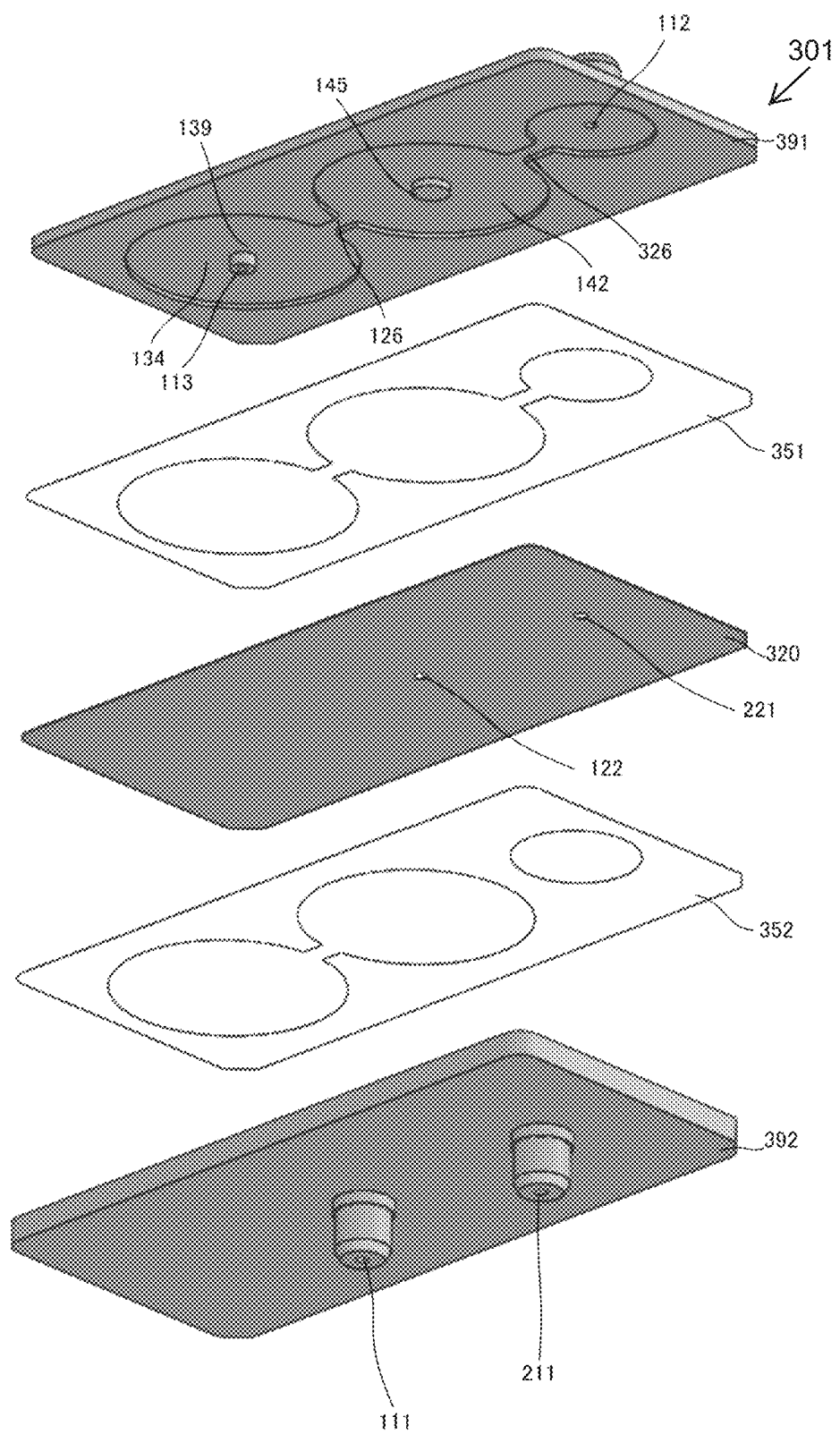
FIG. 16 is an exploded perspective view of the passive valve 101 illustrated in FIG. 13.

FIG. 13 is a descriptive view for explaining a primary part of the fluid control device 300 in the third embodiment of the present disclosure. FIG. 14 is a cross-sectional view of a passive valve 301 illustrated in FIG. 13. FIG. 15 is an exploded perspective view of the passive valve 301 illustrated in FIG. 13. FIG. 16 is an exploded perspective view of the passive valve 301 illustrated in FIG. 13.

The fluid control device 300 is different from the fluid control device 100 in the point that the passive valve 301 includes the check valve 260. The fluid control device 300 is different from the fluid control device 200 in the point that it includes the passive valve 301 formed by integrating the passive valve 101 and the passive valve 201. Other configurations are the same and the description thereof is therefore omitted.

It should be noted that the check valve 260 included in the passive valve 301 and the water-sealing chamber 196 correspond to an example of the "pressure resistance portion" in the present disclosure.

A diaphragm 320 is different from the diaphragm 120 in the point that it includes a hole portion 221. Other configurations are the same and the description thereof is therefore omitted.

A second valve housing 392 has the configuration in which the second valve housing 192 and the second valve housing 292 are integrated. As illustrated in FIG. 14 and FIG. 15, the second valve housing 392 has a wall portion 330 isolating a lower valve chamber 141 and the lower valve chamber 231. Other configurations are the same and the description thereof is therefore omitted.

A first terminal of a tube 337 is connected to the second ventilation hole 112 of the passive valve 301. A second terminal of the tube 337 is connected to the suction hole 14 of the vacuum source 10.

Next, a flow of fluid in the fluid control device 300 will be described.

Figure 17:
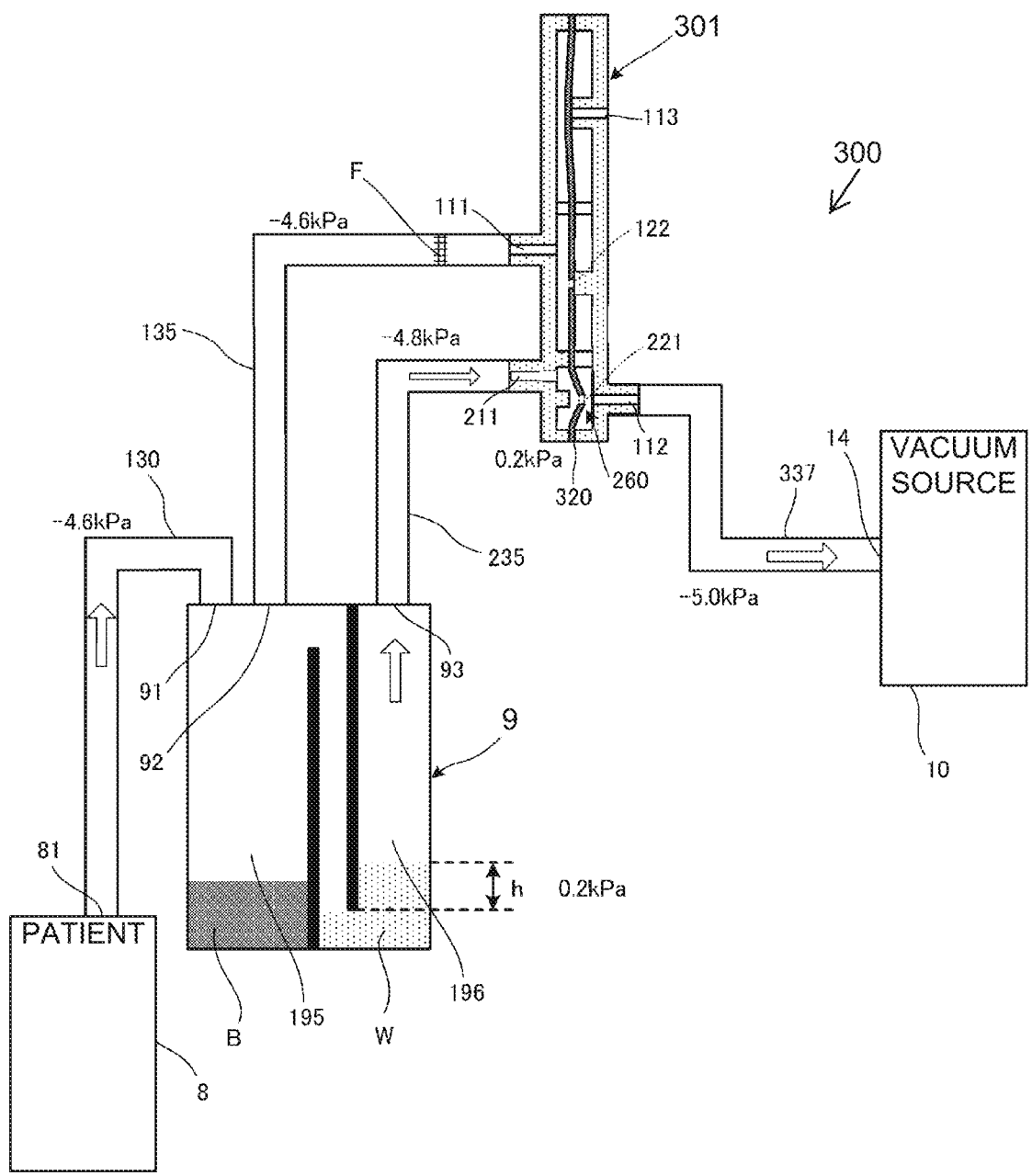
FIG. 17 is a descriptive view for explaining the flow of fluid in the fluid control device 300 while the vacuum source 10 is in ON state.
Figure 18:
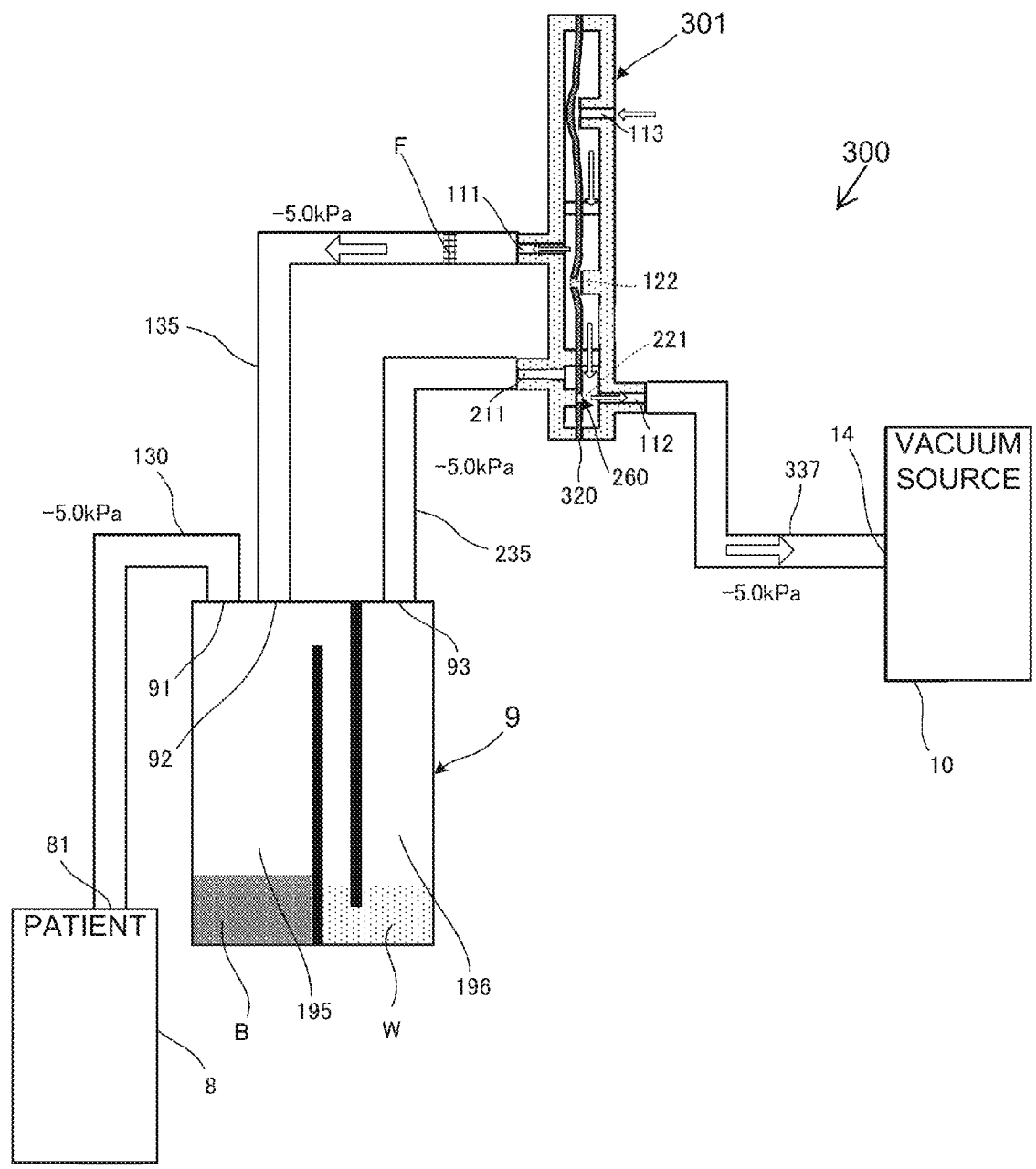
FIG. 18 is a descriptive view for explaining the flow of fluid in the fluid control device 300 immediately after the excess negative pressure is generated in the container 9.

FIG. 17 is a descriptive view for explaining the flow of fluid in the fluid control device 300 while the vacuum source 10 is in ON state. FIG. 18 is a descriptive view for explaining the flow of fluid in the fluid control device 300 immediately after an excess negative pressure is generated in the container 9. Arrows in the drawings indicate flow of the air.

As illustrated in FIG. 17, the gas that has passed through the water-sealing chamber 196 and has flowed out through the third connection hole 93 is sucked into the vacuum source 10 through the suction hole 14 after passing through the check valve 260 of the passive valve 301 while the vacuum source 10 is in ON state.

The check valve 260 of the passive valve 301 and the water-sealing chamber 196 generate a difference between the air pressure in the storage chamber 195 and the air pressure in the suction hole 14. For example, the check valve 260 and the water-sealing chamber 196 generate the difference of 0.4 kPa between the air pressure in the storage chamber 195 and the air pressure in the suction hole 14.

This pressure difference generates, for example, a difference of 0.4 kPa between the air pressure in the first region and the air pressure in the second region in the passive valve 301, as illustrated in FIG. 17. Therefore, the fluid control device 300 can generate the pressure difference in the check valve 260 even when the height h of the water surface varies in the water-sealing chamber 196. Accordingly, the fluid control device 300 can perform a stable operation even when the height h of the water surface varies in the water-sealing chamber 196.

As illustrated in FIG. 18, the flow of fluid in the fluid control device 300 immediately after the excess negative pressure is generated in the container 9 is the same as the flow of fluid in the fluid control device 100, which is illustrated in FIG. 7. Accordingly, the fluid control device 300 also provides the same effects as those of the fluid control device 100.

Furthermore, the passive valve 301 has the configuration in which the passive valve 101 and the passive valve 201 are integrated, the fluid control device 300 can therefore shorten the tube rather than that in the fluid control device 200.

Hereinafter, a fluid control device 400 according to a fourth embodiment of the present disclosure will be described.

Figure 19:
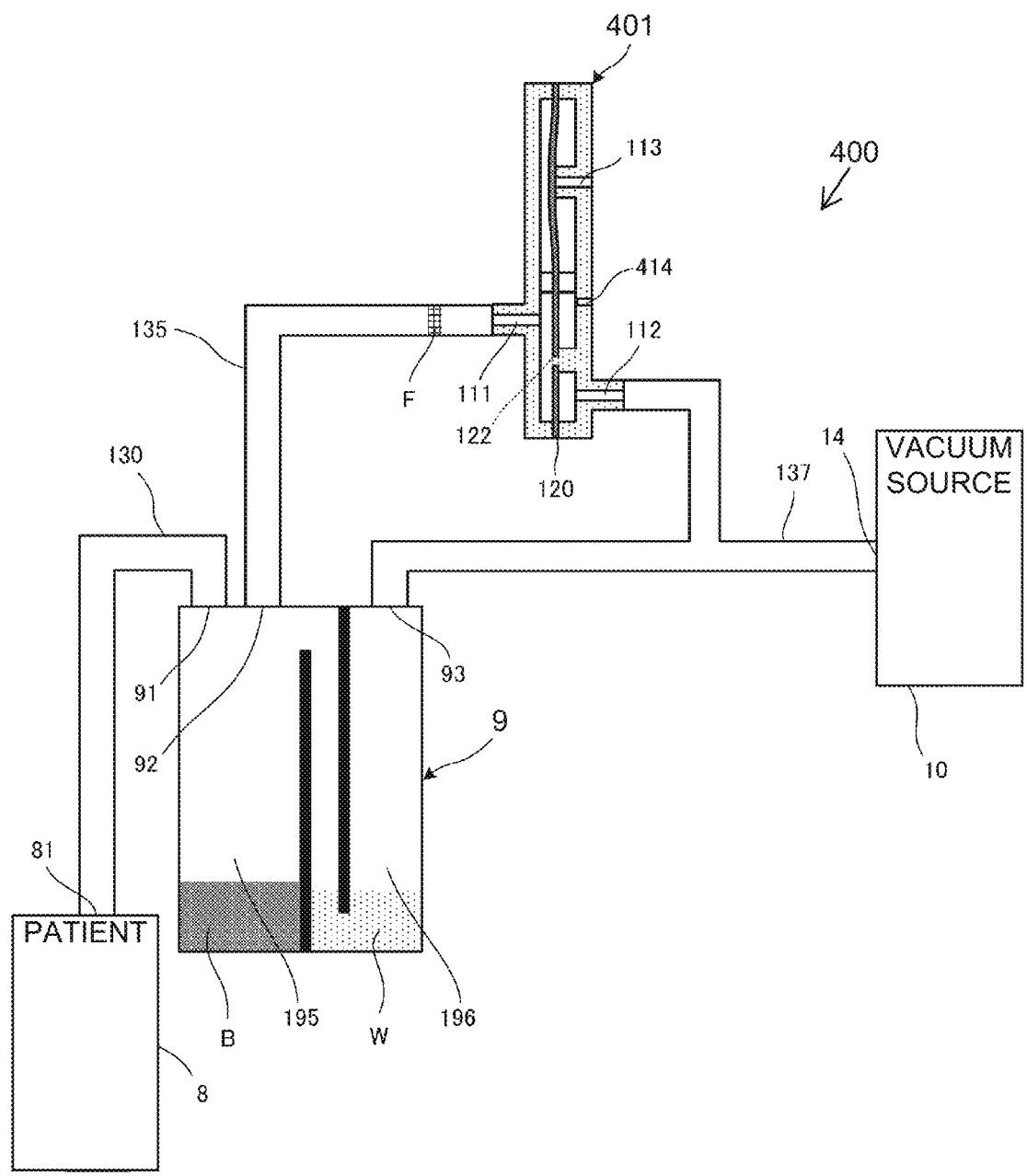
FIG. 19 is a descriptive view for explaining a primary part of a fluid control device 400 according to a fourth embodiment of the present disclosure.
Figure 20:
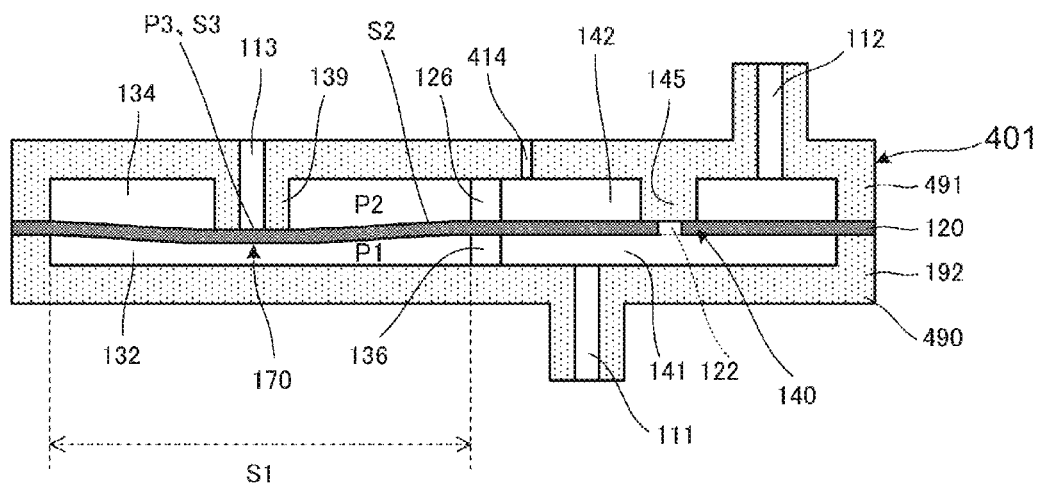
FIG. 20 is a cross-sectional view of a passive valve 401 illustrated in FIG. 19.

FIG. 19 is a cross-sectional view for explaining a primary part of the fluid control device 400 in the fourth embodiment of the present disclosure. FIG. 20 is a cross-sectional view of the passive valve 401 illustrated in FIG. 19. Arrows in the drawings indicate flow of the air.

The fluid control device 400 is different from the fluid control device 100 in the passive valve 401. The passive valve 401 is different from the passive valve 101 in the point that it has a fourth ventilation hole 414. The cross-sectional area of the fourth ventilation hole 414 is extremely smaller than the cross-sectional area of a ventilation path formed in the tube 137. Other configurations of the fluid control device 400 are the same as those of the fluid control device 100 and the description thereof is therefore omitted.

Next, the flow of fluid in the fluid control device 400 will be described.

Figure 21:
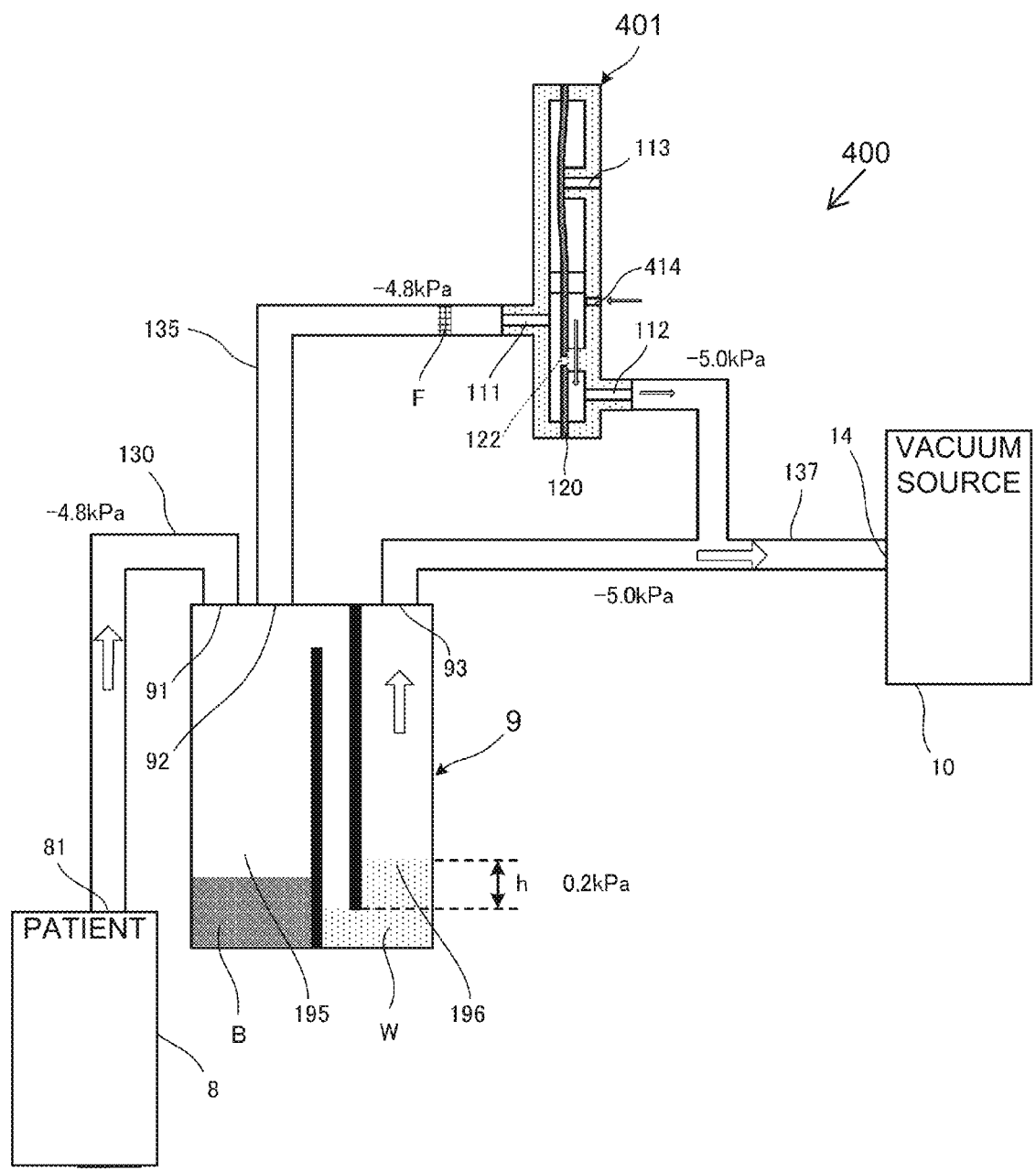
FIG. 21 is a descriptive view for explaining the flow of fluid in the fluid control device 400 while the vacuum source 10 is in ON state.
Figure 22:
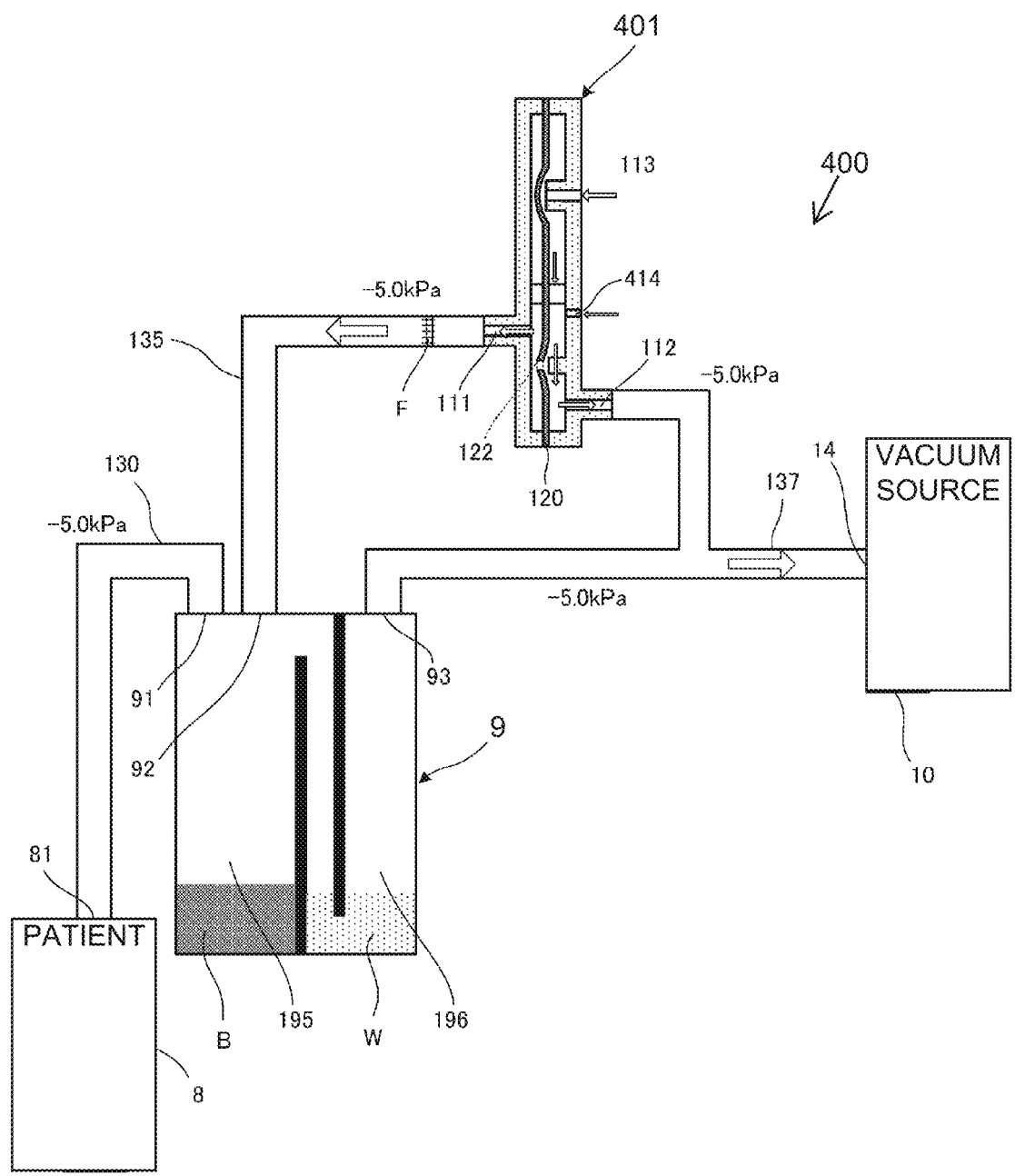
FIG. 22 is a descriptive view for explaining the flow of fluid in the fluid control device 400 immediately after the excess negative pressure is generated in the container 9.

FIG. 21 is a descriptive view for explaining the flow of fluid in the fluid control device 400 while the vacuum source 10 is in ON state. FIG. 22 is a descriptive view for explaining the flow of fluid in the fluid control device 400 immediately after an excess negative pressure is generated in the container 9.

As illustrated in FIG. 21, the gas that has passed through the water-sealing chamber 196 is sucked into the vacuum source 10 through the third connection hole 93 after passing through the ventilation path in the tube 137 while the vacuum source 10 is in ON state.

In this case, the cross-sectional area of the fourth ventilation hole 414 is extremely smaller than the cross-sectional area of the ventilation path in the tube 137 and therefore resulting in less influence. In the passive valve 401, a small amount of the air is taken into the passive valve 401 from the outside of the passive valve 401 through the fourth ventilation hole 414. However, the suction pressure of the vacuum source 10 is hardly lowered. The flow of fluid in the fluid control device 400, while the vacuum source 10 is in ON state is substantially the same as the flow of fluid in the fluid control device 100, which is illustrated in FIG. 5.

The flow of fluid in the fluid control device 400 is different from the flow of fluid in the fluid control device 100 (see FIG. 7) immediately after the excessive negative pressure is generated in the container 9 or immediately after the vacuum source 10 is turned OFF in the above-described intermittent operation.

In the passive valve 401, as illustrated in FIG. 22, a small amount of the air is taken into the passive valve 401 from the outside of the passive valve 401 through the fourth ventilation hole 414 immediately after the excessive negative pressure is generated in the storage chamber 195 in the container 9. Therefore, a speed at which the diaphragm 120 opens the third ventilation hole 113 is increased in the passive valve 401. Accordingly, the fluid control device 400 can rapidly release the excess negative pressure immediately after the excessive negative pressure is generated in the container 9.

On the other hand, in the passive valve 401, a small amount of the air is taken into the passive valve 401 from the outside of the passive valve 401 through the fourth ventilation hole 414 immediately after the vacuum source 10 is turned OFF in the above-described intermittent operation. Therefore, the speed at which the diaphragm 120 opens the third ventilation hole 113 is increased in the passive valve 401. Accordingly, the fluid control device 400 can rapidly release the inside of the container 9 to the atmosphere immediately after the vacuum source 10 is turned OFF.

Other flow of fluid is the same as that in the fluid control device 100 and the description thereof is therefore omitted. The fluid control device 400 also provides the same effects as those of the fluid control device 100.

Other Embodiments

Although only the tube 135 includes the filter F in the above-described embodiments, the embodiment is not limited to this configuration. In implementation, a tube other than the tube 135 may include a filter.

Finally, description of the above-described embodiments is exemplary in all the points and is non-limiting. The scope of the present disclosure is limited by not the above-described embodiments but the appended claims of the disclosure. Furthermore, the scope of the present disclosure encompasses equivalent ranges to the appended claims of the disclosure.

B LIQUID
F FILTER
W WATER
8 PATIENT
9 CONTAINER
10 VACUUM SOURCE
14 SUCTION HOLE
81 INTAKE PORT
91 FIRST CONNECTION HOLE
92 SECOND CONNECTION HOLE
93 THIRD CONNECTION HOLE
100, 200, 300, 400 FLUID CONTROL DEVICE
101, 201, 301, 401 PASSIVE VALVE
111 FIRST VENTILATION HOLE
112 SECOND VENTILATION HOLE
113 THIRD VENTILATION HOLE
120 DIAPHRAGM
122 HOLE PORTION
126 COMMUNICATION PATH
130, 135, 137, 235, 237, 337 TUBE
132 LOWER VALVE CHAMBER
134 UPPER VALVE CHAMBER
136 COMMUNICATION PATH
139 VALVE SEAT
140 CHECK VALVE
141 LOWER VALVE CHAMBER
142 UPPER VALVE CHAMBER
145 VALVE SEAT
151 FIRST SEAL MEMBER
152 SECOND SEAL MEMBER
170 EXHAUST VALVE
190 VALVE HOUSING
191 FIRST VALVE HOUSING
192 SECOND VALVE HOUSING
195 STORAGE CHAMBER
196 WATER-SEALING CHAMBER
209 CONTAINER
211 FIRST VENTILATION HOLE
212 SECOND VENTILATION HOLE
220 DIAPHRAGM
221 HOLE PORTION
231 LOWER VALVE CHAMBER
233 UPPER VALVE CHAMBER
238 VALVE SEAT
260 CHECK VALVE
290 VALVE HOUSING
291 FIRST VALVE HOUSING
292 SECOND VALVE HOUSING
295 STORAGE CHAMBER
320 DIAPHRAGM
330 WALL PORTION
392 SECOND VALVE HOUSING
414 FOURTH VENTILATION HOLE

The invention claimed is:

1. A fluid control device comprising:
a container having a first connection hole, a storage chamber, a second connection hole and a third connection hole, wherein the first connection hole communicates with an inside of a subject, the storage chamber stores a liquid among fluids flowed into the storage chamber through the first connection hole, the second connection hole communicates with the storage chamber, and the third connection hole communicates with a suction hole provided in a vacuum source and a gas among the fluids flows out through the third connection hole;
a pressure resistance portion provided between the storage chamber and the suction hole and generating a difference between an air pressure in the storage chamber and an air pressure in the suction hole; and
a passive valve having a valve housing and a diaphragm, wherein a first ventilation hole, a second ventilation hole and a third ventilation hole are provided in the valve housing, and the diaphragm divides an inside of the valve housing into a first region communicating with the first ventilation hole and a second region communicating with the second ventilation hole,
wherein the first ventilation hole communicates with the second connection hole, the second ventilation hole communicates with the suction hole, and the third ventilation hole communicates with an outside of the valve housing.

2. The fluid control device according to claim 1,
wherein the diaphragm is fixed to the valve housing so as to:
block communication between the first ventilation hole and the second ventilation hole and block communication between the second ventilation hole and the third ventilation hole, when a pressure in the first region is equal to or higher than a pressure in the second region, and
communicate the first ventilation hole and the second ventilation hole and communicate the second ventilation hole and the third ventilation hole, when the pressure in the first region is lower than the pressure in the second region.

3. The fluid control device according to claim 1,
wherein the pressure resistance portion is a water-sealing chamber provided between the storage chamber in the container and the third connection hole.

4. The fluid control device according to claim 1,
wherein the pressure resistance portion is a valve provided between the third connection hole and the suction hole.

5. The fluid control device according to claim 1,
wherein a fourth ventilation hole communicating the second region with the outside of the valve housing is provided in the valve housing.

6. The fluid control device according to claim 5, further comprising a ventilation path connecting the pressure resistance portion to the suction hole,
wherein a cross-sectional area of the fourth ventilation hole is smaller than a cross-sectional area of the ventilation path.

7. The fluid control device according to claim 1, further comprising a filter between the first ventilation hole and the second connection hole.

8. The fluid control device according to claim 2,
wherein the pressure resistance portion is a water-sealing chamber provided between the storage chamber in the container and the third connection hole.

9. The fluid control device according to claim 2,
wherein the pressure resistance portion is a valve provided between the third connection hole and the suction hole.

10. The fluid control device according to claim 2,
wherein a fourth ventilation hole communicating the second region with the outside of the valve housing is provided in the valve housing.

11. The fluid control device according to claim 3,
wherein a fourth ventilation hole communicating the second region with the outside of the valve housing is provided in the valve housing.

12. The fluid control device according to claim 4,
wherein a fourth ventilation hole communicating the second region with the outside of the valve housing is provided in the valve housing.

13. The fluid control device according to claim 2, further comprising a filter between the first ventilation hole and the second connection hole.

14. The fluid control device according to claim 3, further comprising a filter between the first ventilation hole and the second connection hole.

15. The fluid control device according to claim 4, further comprising a filter between the first ventilation hole and the second connection hole.

* * * * *